US009758767B2

(12) United States Patent
Son et al.

(10) Patent No.: US 9,758,767 B2
(45) Date of Patent: Sep. 12, 2017

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Bo Kyung Son, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/767,266

(22) PCT Filed: Feb. 26, 2014

(86) PCT No.: PCT/KR2014/001591

§ 371 (c)(1),
(2) Date: Aug. 11, 2015

(87) PCT Pub. No.: WO2014/133322

PCT Pub. Date: Sep. 4, 2014

(65) Prior Publication Data

US 2016/0076003 A1 Mar. 17, 2016

(30) Foreign Application Priority Data

Feb. 27, 2013 (KR) ........................ 10-2013-0021500

(51) Int. Cl.
*C12N 7/00* (2006.01)
*A61K 35/76* (2015.01)

(52) U.S. Cl.
CPC ................ *C12N 7/00* (2013.01); *A61K 35/76* (2013.01); *C12N 2795/10321* (2013.01); *C12N 2795/10331* (2013.01); *C12N 2795/10332* (2013.01)

(58) Field of Classification Search
None
See application file for complete search history.

(56) References Cited

U.S. PATENT DOCUMENTS

| | | | |
|---|---|---|---|
| 7,625,739 | B2 | 12/2009 | Pasternack et al. |
| 7,625,740 | B2 | 12/2009 | Pasternack et al. |
| 2009/0047727 | A1 | 2/2009 | Pasternack et al. |

FOREIGN PATENT DOCUMENTS

| | | | |
|---|---|---|---|
| EP | 2143729 | A1 | 1/2010 |
| JP | 2005-516618 | A | 6/2005 |
| KR | 10-2009-0021475 | A | 3/2009 |
| KR | 10-0910961 | B1 | 8/2009 |
| KR | 10-2012-0076710 | A | 7/2012 |
| WO | 2012/030535 | A2 | 3/2012 |

OTHER PUBLICATIONS

Miller et al., "Bacteriophage Therapy for Control of Necrotic Enteritis of Broiler Chickens Experimentally Infected with Clostridium perfringens", Avian Diseases, 2010, vol. 54, No. 1, pp. 33-40.

International Search Report dated Apr. 28, 2014 of PCT/KR2014/001591 which is the parent application—4 pages.

Zimmer et al., "Genomic Analysis of Clostridium perfringens Bacteriophage Φ3626, Which Integrates into guaA and Possibly Affects Sporulation", Journal of Bacteriology, Aug. 2002, vol. 184, No. 16, pp. 4359-4368.

Niariya et al., "Identification and characterization of a putative endolysin encoded by episomal phage phiSM101 of Clostridium perfringens", Applied Microbiology and Biotechnology, 2011, vol. 90, pp. 1973-1979.

Zimmer et al., "The Murein Hydrolase of the Bacteriophage Φ3636 Dual Lysis System is Active against All Tested Clostridium perfringens Strains", Applied and Environmental Microbiology, Nov. 2002, vol. 68, No. 11, pp. 5311-5317.

Hermoso et al., "Taking aim on bacterial pathogens: from phage therapy to enzybiotics", Current Opinion in Microbiology, 2007, vol. 10, pp. 461-472.

Extended European Search Report dated Jun. 30, 2016 of European Patent Application No. 14757316.6—6 pages.

Morinigo et al., "Evaluation of Different Bacteriophage Groups as Faecal Indicators in Contaminated Natural Waters in Southern England", Wat. Res. 1992, vol. 26, No. 3, pp. 267-271.

Cislo M, et al., "Archivum Immunologiae et Therapiae Experimentalis", Ther. Exp. 2:175-183, 1987.

*Primary Examiner* — Nicole Kinsey White
(74) *Attorney, Agent, or Firm* — Knobbe Martens Olson & Bear LLP

(57) ABSTRACT

Provided is a novel bacteriophage ΦCJ22 (KCCM11364P). In addition, provided is an antibacterial composition containing the bacteriophage ΦCJ22 (KCCM11364P) as an active ingredient. Further, provided is a method of preventing and/or treating infectious diseases caused by *Clostridium perfringens* in animals except for humans by using the bacteriophage ΦCJ22 (KCCM11364P) or an antibacterial composition containing the bacteriophage ΦCJ22 (KCCM11364P) as an active ingredient.

7 Claims, 3 Drawing Sheets

BACTERIOPHAGE AND ANTIBACTERIAL COMPOSITION COMPRISING THE SAME

CROSS REFERENCE TO RELATED APPLICATIONS

This application is the U.S. National Phase Application under 35 U.S.C. §371 of International Application No. PCT/KR2014/001591, filed Feb. 26, 2014, designating the U.S. and published as WO 2014/133322 Ab1 on Sep. 4, 2014 which claims the benefit of Korean Patent Application No. KR-10-2013-0021500, filed Feb. 27, 2013. Any and all applications for which a foreign and/or a domestic priority is claimed is/are identified in the Application Data Sheet filed herewith and is/are hereby incorporated by reference in their entirety under 37 C.F.R. §1.57.

REFERENCE TO SEQUENCE LISTING

This application incorporates by reference the sequence listing submitted as ASCII text filed via EFS-Web on Aug. 11, 2015, and updated by a file entitled "AIP22.012APC_REPLACEMENT_SEQLIST.txt" which is 68,324 bytes in size, created on Nov. 19, 2015, and last modified on Nov. 25, 2015.

TECHNICAL FIELD

The present invention relates to a novel bacteriophage having a specific bactericidal activity against pathogenic *Clostridium perfringens* and an antibacterial composition comprising the same. In addition, the present invention relates to a method of preventing or treating animal diseases using the novel bacteriophage or the antibacterial composition.

BACKGROUND ART

*Clostridium perfringens* (CP), which is gram-positive large obligatory anaerobic *bacillus*, has been known as a bacterium that does not have flagellum and forms a spore. *Clostridium perfringens*, which is a bacterium causing diarrhea, or the like, particularly, in domestic animals such as chicken, pork, and the like, has been recognized as one of the important and fatal pathogenic bacteria followed closely in a livestock industry, such as *Salmonella* causing fowl typhoid.

Currently, one of the diseases frequently generated in poultry and pork industries is necrotic enteritis by *Clostridium perfringens*. It is known that necrotic enteritis is frequently generated by co-infection of *Clostridium perfringens* and *coccidium*, and as a main symptom of necrotic enteritis, there is bloody diarrhea due to severe necrotic lesions in a lower portion of small intestine of chickens, swines, or the like.

This necrotic enteritis generates dehydration symptom, periodic diarrhea, and the like, in an infected animal according to the disease severity, gradually debilitates a body of the animal, and causes growth retardation, and the like, such that necrotic enteritis has become a significant problem in the livestock industry. Further, since *Clostridium perfringens* is easily propagated through feces of animal, transmission between animals in a common breeding space may be easily generated by oral infection through soil or contaminated feed, or the like. Particularly, incidence in young animal is high, such that *Clostridium perfringens* has become a problem.

Meanwhile, bacteriophage is a specialized type of virus that infects and destroys only bacteria, and can self-replicate only inside host bacteria. The bacteriophage has strong host specificity as compared to antibiotics, and recently, a problem of emergence of strain resistant against antibiotics has been serious, such that an interest in practical use of the bacteriophage has increased (Non-Patent Documents 1 and 2).

Therefore, research into the bacteriophage has been actively conducted in various countries around the world, and in addition to a patent application for bacteriophage, an attempt to acquire Food and Drug Administration (FDA) approval for a composition containing the bacteriophage has been gradually increased.

As the related art documents for the bacteriophage, a bacteriophage having a specific bactericidal activity against *Clostridium perfringens* has been disclosed in Patent Document 1, and a bacteriophage having a specific bactericidal activity against *Staphylococcus aureus* has been disclosed in Patent Document 2. Further, lytic protein derived from a bacteriophage specifically destroying peptidoglycan structure of bacterial cell membrane, and bacteria lysates by the lytic protein have been disclosed in Patent Document 3.

However, in spite of presence of the following related arts, a technology associated with the bacteriophage for preventing and/or treating infectious diseases, particularly, necrotic enteritis by *Clostridium perfringens* that is a still important problem in the livestock industry including the poultry and pork industries is still insufficient, such that a bacteriophage and a technology associated with the bacteriophage should be developed.

RELATED ART DOCUMENT

Patent Document (Patent Document 1) Korean Patent Laid-open Publication No. 10-2012-0076710 A (Patent Document 2) Korea Patent Registration Publication No. 10-0910961 B1

(Patent Document 3) Korean Patent Laid-Open Publication No. 10-2009-0021475 A

Non-Patent Document (Non Patent Document 1) Cislo M, et al., Arch. Immunol. Ther. Exp. 2:175-183, 1987

(Non Patent Document 2) Sung Hun Kim et al, Bacteriophage, Novel Alternative Antibiotics, BioWave Vol. 7 No. 15, 2005, BRIC

DISCLOSURE

Technical Problem

The present inventors conducted studies in order to solve problems such as resistant bacteria occurring upon the use of antibiotics, antibiotics remaining in meat, and the like, and efficiently prevent and treat infectious diseases by *Clostridium perfringens*, and as a result, the present inventors isolated new bacteriophage ΦCJ22 (KCCM11364P) having a specific bactericidal activity against *Clostridium perfringens* from nature.

In addition, the present inventors identified morphological, biochemical, and genetic characteristics of the novel bacteriophage and confirmed that the bacteriophage had excellent acid resistance, heat resistance, drought resistance, and the like, thereby developing an antibiotic, a disinfectant, a feed additive, and other compositions using the novel bacteriophage. Further, the present inventors developed a composition for preventing or treating infectious diseases by *Clostridium perfringens* and a method of preventing or treating the disease using the composition.

The present invention provides a novel bacteriophage ΦCJ22 (KCCM11364P) having a specific bactericidal activity against *Clostridium perfringens.*

In addition, the present invention provides a composition for preventing and/or treating infectious diseases by *Clostridium perfringens* containing the bacteriophage ΦCJ22 (KCCM11364P) as an active ingredient.

Further, the present invention provides provide an antibiotic, a feed additive, a drinking water additive, a disinfectant, or a cleaner containing the bacteriophage ΦCJ22 (KCCM11364P) as an active ingredient.

Furthermore, the present invention provides a method of preventing and/or treating infectious diseases by *Clostridium perfringens* in animals except for humans using the bacteriophage ΦCJ22 (KCCM11364P) or a composition containing the bacteriophage ΦCJ22 (KCCM11364P) as an active ingredient.

Technical Solution

According to an exemplary embodiment of the present invention, there is provided a novel bacteriophage ΦCJ22 (KCCM11364P) having a specific bactericidal activity against *Clostridium perfringens.*

According to another exemplary embodiment of the present invention, there is provided a composition for preventing or treating an infectious disease caused by *Clostridium perfringens*, the composition containing the bacteriophage ΦCJ22 (KCCM11364P) as described above as an active ingredient.

According to another exemplary embodiment of the present invention, there are provided an antibiotic, a feed additive, a drinking water additive, a disinfectant, or a cleaner containing the bacteriophage ΦCJ22 (KCCM11364P) as described above as an active ingredient.

According to another exemplary embodiment of the present invention, there is provided a method of preventing or treating an infectious disease caused by *Clostridium perfringens*, comprising administering the bacteriophage ΦCJ22 (KCCM11364P) or the composition containing the bacteriophage ΦCJ22 as described above to animals except for humans.

Advantageous Effects

The bacteriophage ΦCJ22 (KCCM11364P) according to the present invention may have the specific bactericidal activity against *Clostridium perfringens.*

In addition, the bacteriophage ΦCJ22 (KCCM11364P) according to the present invention has excellent acid resistance, heat resistance, and drought resistance, such that the bacteriophage ΦCJ22 (KCCM11364P) may be used as a material for preventing or treating infectious diseases by *Clostridium perfringens* in various temperature or pH ranges, under moisture conditions, and the like, and utilized as an antibiotic, a feed additive, a drinking water additive, a disinfectant, a cleaner, or the like.

Further, according to the present invention, infectious diseases by *Clostridium perfringens* may be prevented or treated by administering the bacteriophage ΦCJ22 (KCCM11364P) or a composition containing the bacteriophage ΦCJ22 (KCCM11364P) as an active ingredient to animals except for human.

BEST MODE

Hereinafter, the present invention will be described in detail. Since contents that are not described in the present specification may be sufficiently recognized and inferred by those skilled in the art or similar art, a description thereof will be omitted.

In one general aspect, the present invention provides a novel bacteriophage ΦCJ22 (KCCM11364P) having a specific bactericidal activity against *Clostridium perfringens* (CP).

It is known that *Clostridium perfringens*, which is gram-positive large obligatory anaerobic *bacillus*, does not have a flagellum and forms a spore. *Clostridium perfringens*, which is a bacterium causing diarrhea, or the like, in animals, particularly, in domestic animals such as poultry, swine, and the like, has been recognized as one of the dangerous and fatal pathogenic bacteria in a livestock industry as *Salmonella* causing fowl typhoid.

A bacteriophage is a bacteria-specific virus infecting specific bacteria to suppress and inhibit growth of the bacteria and means a virus including single or double stranded deoxyribonucleic acid (DNA) or ribonucleic acid (RNA) as a genetic material.

Figure 1:
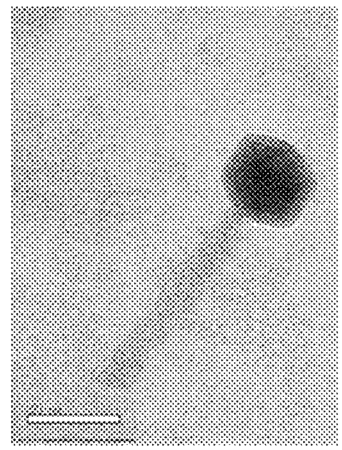
FIG. 1 is an electron microscope photograph of a novel bacteriophage ΦCJ22 (KCCM11364P, hereinafter, referred to as 'ΦCJ22').

A bacteriophage ΦCJ22 of the present invention, which is a bacteriophage having species-specificity of selectively infecting *Clostridium perfringens*, is a bacteriophage that has an isometric capsid and a non-contractile tail, and morphologically belongs to *Siphoviridae* (FIG. 1). Homology analysis data of nucleic acid sequences between bacteriophage ΦCJ22 and other bacteriophages is shown in table 1. Activity of bacteriophage ΦCJ22 was stable for 2 hours at the range from pH 4 to pH 9.8 (acid resistance, see FIG. 4). ΦCJ22 retained its activity for 2 hours when it was exposed at 60° C. (heat resistance, see FIG. 5), and its titer was decreased about 2 log after drying (see FIG. 6). The nucleic acid sequence of bacteriophage ΦCJ22 is the same as SEQ ID NO: 1.

The bacteriophage ΦCJ22, which was a bacteriophage newly isolated by the present inventors, was deposited at Korean Culture Center of Microorganisms (361-221, Hongjedong, Seodamun-gu, Seoul, Korea) as a deposition number KCCM11364P on Jan. 30, 2013.

In another general aspect, the present invention provides a composition for preventing or treating infectious diseases by *Clostridium perfringens* containing the bacteriophage ΦCJ22 as an active ingredient. As a preferable example of the composition, the present invention provides an antibiotic.

Since the bacteriophage ΦCJ22 has an antibacterial activity capable of specifically killing *Clostridium perfringens*, the bacteriophage ΦCJ22 may be used to prevent or treat diseases generated by infection of *Clostridium perfringens*. As a suitable example of the infectious disease caused by *Clostridium perfringens* capable of being treated using the bacteriophage ΦCJ22, there is necrotic enteritis, but the present invention is not limited thereto.

Necrotic enteritis, which is one of the main infectious diseases caused by *Clostridium perfringens*, corresponds to a bacterial disease most frequently generated in domestic animals, particularly, poultry and causes significant damage. The disease may be generated in poultry, especially chickens substantially at all ages, but is mainly generated in chickens (2 to 5 weeks old) bred on the floor and also frequently generated in chickens (12 to 16 weeks old) bred in a cage.

As *Clostridium perfringens* is excessively proliferated in the small intestine, symptoms of necrotic enteritis are generated, and necrosis of gastrointestinal mucosa, sudden diarrhea, and the like, are caused. For example, in swines, in the case of very acute necrotic enteritis, after 1 to 2 days of occurrence, mortality of the swine is generated, and in the case of acute necrotic enteritis, after 2 to 3 days of bloody diarrhea, mortality of the swine is generated. Further, in the case of sub-acute necrotic enteritis, diarrhea (there is no bloody feces) proceeds for 5 to 7 days, and then weakness and dehydration are caused, and in the case of chronic necrotic enteritis, intermittent diarrhea is caused, and growth disorder may be generated.

The term "prevention" as used herein refers to all actions of providing the bacteriophage ΦCJ22 and/or the composition containing the bacteriophage ΦCJ22 as the active ingredient to animals except for humans to suppress the corresponding disease or retard disease occurring.

The term "treatment" as used herein refers to all actions of providing the bacteriophage ΦCJ22 and/or the composition containing the bacteriophage ΦCJ22 as the active ingredient to animals except for humans to thereby allow the symptom of the corresponding disease caused by infection to get better or be alleviated.

As an example of the infectious disease caused by *Clostridium perfringens* to which the bacteriophage ΦCJ22 and/or the composition containing the bacteriophage ΦCJ22 as the active ingredient may be applied, there is necrotic enteritis, but the present invention is not limited thereto.

The composition for preventing or treating the infectious diseases caused by *Clostridium perfringens* according to the present invention may contain the bacteriophage ΦCJ22 at a content of preferably $5\times10^2$ to $5\times10^{12}$ pfu/ml, more preferably, $1\times10^6$ to $1\times10^{10}$ pfu/ml.

The composition for preventing or treating infectious diseases by *Clostridium perfringens* according to the present invention may further contain a pharmaceutically acceptable carrier and be formulated together with the carrier to thereby be provided as food, a drug, a feed additive, a drinking water additive, and the like.

The term "pharmaceutically acceptable carrier" as used herein means a carrier or a diluent that does not stimulate living organism nor inhibit biological activity and properties of an administered compound.

A kind of carrier usable in the present invention is not particularly limited, and any carrier may be used as long as it is generally used in the art and is pharmaceutically acceptable. As a non-restrictive example of the carrier, there are normal saline, sterile water, buffered saline, Ringer's solution, an albumin injection solution, a dextrose solution, a maltodextrin solution, glycerol, ethanol, and the like. One or a mixture of at least two of these carriers may be used.

In addition, if necessary, another general additive such as an antioxidant, a buffer, a bacteriostatic agent, and/or the like, may be further added and used, and the composition may be formulated into an injection formulation such as an aqueous solution, suspension, emulsion, or the like, pills, capsules, granules, tablets, or the like by additionally adding a diluent, a dispersant, a surfactant, a binder, a lubricant, and/or the like, and then used.

An administration method of the composition for preventing or treating infectious diseases by *Clostridium perfringens* is not particularly limited, but any method generally used in the art may be used. As a non-restrictive example of the administration method, the composition may be orally or parenterally administered.

As a non-restrictive example of the formulation for oral administration, there are troches, lozenge, tablets, aqueous suspensions, oily suspensions, prepared powder, granules, emulsions, hard capsules, soft capsules, syrups, elixirs, or the like.

In order to formulate the composition according to the present invention into a formulation such as a tablet, a capsule, or the like, the formulation may further contain a binder such as lactose, saccharose, sorbitol, mannitol, starch, amylopectin, cellulose, gelatin; an excipient such as dicalcium phosphate, or the like; a disintegrant such as corn starch, sweet potato starch, or the like; a lubricant such as magnesium stearate, calcium stearate, sodium stearyl fumarate, polyethylene glycol wax, or the like. In the case of the capsule formulation, the formulation may additionally contain a liquid carrier such as fatty oil in addition to the above-mentioned materials.

As a parenteral administration method, an intravenous administration method, an intraperitoneal administration method, an intramuscular administration method, a subcutaneous administration method, a local administration method, or the like, may be used. In addition, a method of applying or spraying the composition onto a disease site may also be used, but the present invention is not limited thereto.

An example of the formulation for parenteral administration may include injection formulations for subcutaneous injection, intravenous injection, intramuscular injection, or the like; suppository formulations; spray formulations such as aerosol formulations capable of being inhaled through respiratory system, or the like, but the present invention is not limited thereto. In order to formulate the composition into the injection formulation, the composition according to the present invention may be mixed with a stabilizer or a buffer in water to thereby prepare a solution or suspension, and then, the prepared solution or suspension may be formulated in a unit dose for an ampoule or vial. In the case of formulating the composition into the spray formulation such as the aerosol formulation, or the like, a propellant, or the like, may be mixed together with an additive so that a water-dispersed condensate or wet powder is dispersed.

A suitable application, spray, or administration dose of the composition for preventing or treating infectious diseases by *Clostridium perfringens* may be variously determined depending on factors such as age, weight, sex, degree of symptoms of disease, a kind of food, excretion rate of administration target animals, or the like, as well as a method of formulating the composition, an administration method, an administration time and/or route. Generally, a veterinarian having ordinary skill in the art may easily determine and prescribe an effective dose for the desired treatment.

In another general aspect, the present invention may provide an antibiotic containing the bacteriophage ΦCJ22 as an active ingredient.

The term "antibiotic" as used herein means an agent capable of being provided to animals including humans in a drug form to thereby kill bacteria, and corresponds to a concept collectively indicating a preservative, a disinfectant, and an antibacterial agent.

The antibiotic containing the bacteriophage ΦCJ22 according to the present invention as the active ingredient may have high specificity to *Clostridium perfringens* as compared to an antibiotic according to the related art to thereby not kill beneficial bacteria but kill specific pathogenic bacteria, and does not induce drug resistance, such that the antibiotic according to the present invention may be provided as a novel antibiotic having an elongated lifespan as compared to the antibiotic according to the related art.

In another general aspect, the present invention may provide a feed additive and a drinking water additive containing the bacteriophage ΦCJ22 as an active ingredient.

The feed additive and the drinking water additive according to the present invention may be used in a manner in which the bacteriophage ΦCJ22 or the composition containing the bacteriophage ΦCJ22 is individually prepared in a feed additive or drinking water additive form and then mixed with a feed or drinking water, or in a manner in which the bacteriophage ΦCJ22 or the composition containing the bacteriophage ΦCJ22 is directly added at the time of preparing the feed or the drinking water.

The bacteriophage ΦCJ22 or the composition containing the bacteriophage ΦCJ22 used as the feed additive or drinking water additive according to the present invention may be in a liquid state or dried state, and preferably, in a dried powder form.

A drying method for preparing the feed additive and the drinking water additive according to the present invention in the dried powder form is not particularly limited, but a method generally used in the art may be used. As a non-restrictive example of the drying method, there is a natural air drying method, natural drying method, a spray drying method, a freeze-drying method, or the like. One method of these methods may be used alone or at least two methods may be used together with each other.

Another non-pathogenic microbe may be additionally added to the feed additive or drinking water additive. A non-restrictive example of the microbe capable of being added may be selected from a group consisting of *bacillus* sp. capable of producing protease, lipase, and/or sugar converting enzyme such as *bacillus subtilis*, or the like; *Lactobacillus* sp. having physiological activity and degradation activity for an organic material under anaerobic conditions such as cow's stomach; mold fungi having effects of increasing a weight of domestic animal, a milk yield, and digestibility of the feed such as *Aspergillus oryzae*, or the like; and yeasts such as *Saccharomyces cerevisiae*, or the like. One or a mixture of at least two of these microbes may be used.

The feed additive or the drinking water additive containing the bacteriophage ΦCJ22 according to the present invention as the active ingredient may further contain other additives, as needed. As a non-restrictive example of the usable additive, there are a binder, an emulsifier, a preservative, and the like, which are added in order to prevent quality of the feed or driving water from being deteriorated; amino acids, vitamins, enzymes, probiotics, flavoring agents, non-protein nitrogen compounds, silicates, buffers, coloring agents, extractants, oligosaccharides, and the like, which are added in order to increase utility of the feed or drinking water. Otherwise, the additive may further include a feed mixing agent, or the like. One or a mixture of at least two of these additives may be used.

The feed additive may be contained at a content of 0.05 to 10, more preferably 0.1 to 2 parts by weight based on 100 parts by weight of the feed. The drinking water additive may be contained at a content of 0.0001 to 0.01, more preferably 0.001 to 0.005 parts by weight based on 100 parts by weight of the drinking water. The activity of the bacteriophage ΦCJ22 against *Clostridium perfringens* may be sufficiently exhibited in the above-mentioned range.

In another general aspect, the present invention provides a feed or drinking water prepared by adding a feed additive or a drinking water additive containing the bacteriophage ΦCJ22 as an active ingredient or directly adding the bacteriophage ΦCJ22.

The feed used in the present invention is not particularly limited, but any feed generally used in the art may be used. A non-restrictive example of the feed may include plant feeds such as grains, roots and fruit, food processing byproducts, algaes, fiber, pharmaceutical byproducts, fats, starches, cucurbitaceous, or grain byproducts; and animal feeds such as proteins, inorganic materials, fats, minerals, single cell proteins, animal planktons, or foods. One or a mixture of at least two of these feeds may be used.

The drinking water used in the present invention is not particularly limited, but any drinking water generally used in the present invention may be used.

In another general aspect, the present invention may provide a disinfectant or a cleaner containing the bacteriophage ΦCJ22 as an active ingredient. A formulation of the disinfectant or cleaner is not particularly limited, but the disinfectant or cleaner may be formulated into any formulation known in the art.

The disinfectant may be sprayed in order to remove *Clostridium perfringens* onto a region in which animals live, a slaughterhouse, a mortality generation area, a cooking place or cooking equipment, or the like, but the present invention is not limited thereto.

The cleaner may be used to wash skin's surfaces or each of the sites of bodies of animals, particularly, poultry or swines, exposed or to be exposed to *Clostridium perfringens*, but the present invention is not limited thereto.

In another general aspect, the present invention provides a method of preventing or treating infectious diseases caused by *Clostridium perfringens* by using the bacteriophage ΦCJ22 or the composition containing the bacteriophage ΦCJ22 as an active ingredient. The infectious disease may be preferably necrotic enteritis, but the present invention is not limited thereto. The target of preventing or treating infectious disease caused by *Clostridium perfringens* may be a poultry or swine, but the present invention is not limited thereto.

In detail, the method of preventing or treating infectious diseases according to the present invention may include administering the bacteriophage ΦCJ22 or the composition comprising the bacteriophage ΦCJ22 as the active ingredient to targets infected by *Clostridium perfringens* or being at risk of infection of *Clostridium perfringens* except for humans in a pharmaceutically effective dose. It will be apparent to those skilled in the art that when the pharmaceutical composition is administered to patient, the suitable total daily dose may be determined by an attending physician or veterinarian within the scope of sound medical judgement.

A specific pharmaceutically effective dose of the bacteriophage ΦCJ22 or the composition containing the bacteriophage ΦCJ22 as the active ingredient for a specific animal may be determined by considering an administration time and an administration route of the bacteriophage ΦCJ22 or the composition containing the bacteriophage ΦCJ22, a secretion rate of the composition, a therapy duration period, or the like, in addition to a kind and a degree of the desired response, an age, a weight, a general healthy state, sex, or diet of the corresponding individual. In addition, the pharmaceutically effective dose may be variously changed according to various factors such as ingredients of drugs or other compositions simultaneously or separately used and similar factors well known in a medical field.

The bacteriophage ΦCJ22 according to the present invention or the composition containing the bacteriophage ΦCJ22 as the active ingredient may be administered as a pharmaceutical form (nasal spray) to animals or administered in a method of directly added to a feed or drinking water of the animals and then feeding the feed or drinking water. In addition, the bacteriophage ΦCJ22 or the composition containing the same may be mixed in a feed or drinking water in a form of a feed additive or drinking water additive and then administered.

The administration route and administration method of the bacteriophage ΦCJ22 according to the present invention or the composition containing the bacteriophage ΦCJ22 as the active ingredient are not particularly limited, but any administration route and administration method may be used as long as the bacteriophage ΦCJ22 or the composition containing the same may arrive at the corresponding target tissue. That is, the bacteriophage ΦCJ22 or the composition containing the bacteriophage ΦCJ22 as the active ingredient may be administered through various oral or parenteral routes. As a non-restrictive example of the administration route, oral, rectal, local, intravenous, intraperitoneal, intramuscular, intraarterial, subcutaneous, and nasal administration, inhalation, or the like, may be performed.

Hereinafter, the present invention will be described in detail through the Examples. However, these Examples are only to illustrate the present invention, and a scope of the present invention is not limited to these Examples.

EXAMPLE 1

Isolation of Bacteriophage Infecting *Clostridium perfringens*

EXAMPLES 1-1

Screening of Bacteriophage and Isolation of Single Bacteriophage

After 50 ml of a sample isolated from a feces sample of Samwhaw Gps. Breeding Agri. Inc., which is a chicken and swine farm in South Chungchong Province, was moved a centrifuge bottle and centrifuged at 4,000 rpm for 10 minutes, the supernatant was filtered with a 0.45 μm filter to prepare a sample solution, and then a soft agar overlay method was performed using the prepared sample solution. The soft agar overlay method is a method of observing a lysis action of bacteriophage using host cells growing in top agar (attached onto a solid medium using 0.7% agar).

In detail, 18 ml of sample filtrates was mixed with 150 μl of a shake culture solution ($OD_{600}$=2) of *Clostridium perfringens*, (CP, BCCP 17-1) isolated at Animal and Plant Quarantine Agency and 2110 of 10× Brain-heart infusion (hereinafter, 'BHI' medium (composed so as to have a final volume of 1 L) and cultured at 37° C. for 18 hours. Then, the culture solution was centrifuged at 4,000 rpm for 10 minutes, and the supernatant was filtered using the 0.45 μm filter.

Thereafter, after a mixture of 5 ml of 0.7% agar (w/v) and 150 μl of the shake culture solution ($OD_{600}$=2) of *Clostridium perfringens* (BCCP 17-1) was poured and hardened into a BHI plate (BHI+0.2% sheep blood), 10 μl of the sample culture filtrate solution was dropped thereon, followed by culturing at 30° C. for 18 hours. Then, it was confirmed that a plaque was formed.

After the sample culture filtrate solution in which lysis was generated was appropriately diluted and mixed with 150 μl of the shake culture solution ($OD_{600}$=2) of *Clostridium perfringens* (BCCP 17-1), the soft agar overlay method was performed, thereby obtaining a single plaque. Since it is considered that a single plaque is formed of a single bacteriophage, in order to purify and isolate the single bacteriophage, a single plaque was selected, put into 400 μl of a SM solution (NaCl (5.8 g/l); $MgSO_4 7H_2O$ (2 g/l); 1 M Tris-Cl (pH 7.5, 50 ml); $H_2O$, composed so as to have a final volume of 1 L), and left at room temperature for 4 hours, thereby purifying and isolating the single bacteriophage.

In order to secure a large amount of the isolated bacteriophage, 100 μl of a supernatant of a single bacteriophage solution was selected and mixed with 12 ml of 0.7% agar and 500 μl of the shake culture solution of *Clostridium perfringens* (BCCP 17-1), followed by performing the soft agar overlay method in a LB medium having a diameter of 150 mm. After pouring 15 ml of the SM solution into a plate in which lysis was completely generated, the plate was softly shaken at room temperature for 4 hours, thereby discharging the bacteriophage in the top-agar. The SM solution in which the bacteriophage was discharged was recovered, and chloroform was added thereto at an amount of 1% of the final volume and suitably mixed for 10 minutes, followed by centrifugation at 4,000 rpm for 10 minutes. The supernatant obtained as described above was filtered with a 0.45 μm filter and stored at a cold temperature.

EXAMPLES 1-2

Large Scale Culture and Purification of Bacteriophage

The selected bacteriophage was cultured at large scale using *Clostridium perfringens* (BCCP 17-1), and then the bacteriophage was purified therefrom.

In detail, 1% of the shake culture solution of *Clostridium perfringens* (BCCP 17-1) was inoculated into a liquid culture medium for mass production, and at the same time, the bacteriophage was put thereinto at multiplicity of infection (MOI) of 0.1, simultaneously with the inoculation of *Clostridium perfringens* (BCCP 17-1), thereby performing co-infection. Then, static culture was performed at 30° C. under anaerobic conditions.

Thereafter, centrifugation was performed at 4° C. and 12,000 rpm for 20 minutes, and then the supernatant was filtered with a 0.45 μm filter. After NaCl and polyethylene glycol (PEG) were added to the filtered supernatant so as to have final concentrations of 1M and 10% (w/v), respectively, and mixed with each other, the mixture was further left at 4° C. for 8 hours or more. Next, after centrifugation was performed at 4° C. and 12,000 rpm for 20 minutes, then the supernatant was removed, and the precipitates were obtained.

The obtained precipitate was resuspended using 5 ml of the SM solution and was left at room temperature for 20 minutes. Thereafter, the supernatant was filtered with a 0.45 μm filter, and ultracentrifugation (35,000 rpm, 1 hour, 4° C.) using a glycerol density gradient method (density: 40%, 5% glycerol) was performed, thereby purifying the bacteriophage ΦCJ22. After the purified ΦCJ22 was resuspended using 500 μl of the SM solution, a titer was measured.

The present inventor called the bacteriophage obtained by extracting the sample from feces and having the specific bactericidal activity against *Clostridium perfringens* "Bacteriophage ΦCJ22" and deposited the bacteriophage at Korean Culture Center of Microorganisms (361-221, Hongjedong, Seodamun-gu, Seoul, Korea) as a deposition number KCCM11364P on Jan. 30, 2013.

EXAMPLE 2

Morphology Observation ΦCJ22

The purified bacteriophage ΦCJ22 was diluted in a 0.01% gelatin solution and then fixed by a 2.5% glutaraldehyde solution. The fixed bacteriophage was dropped onto a carbon-coated mica plate (ca. 2.5×2.5 mm), adapted thereto for 10 minutes, and washed with sterile distilled water. A carbon film was mounted on a copper grid, stained with 4% uranyl acetate for 30 to 60 seconds, dried, and investigated using a transmission electron microscope (JEM-1011, 80 kV, magnification: ×120,000 to ×200,000) (FIG. 1).

FIG. 1 shows an electron microscope photograph of the bacteriophage ΦCJ22, and it may be appreciated that since the bacteriophage does not have an isometric capsid and a contractile tail, the bacteriophage morphologically belongs to *Siphoviridae.*

EXAMPLE 3

Genomic DNA Size Analysis of ΦCJ22

Genomic DNA was extracted from the bacteriophage ΦCJ22 purified by the ultracentrifugation.

In detail, ethylenediaminetetraacetic acid (EDTA, pH 8.0), proteinase K, and sodium dodecyl sulfate (SDS) were added to a culture solution of the purified bacteriophage ΦCJ22 so as to have final concentrations of 20 mM, 50 μg/ml, and 0.5% (w/v), respectively and then, were left at 50° C. for 1 hour. Thereafter, an equal volume of phenol (pH 8.0) was added thereto and stirred, followed by centrifugation at room temperature and 12,000 rpm for 10 minutes, thereby obtaining a supernatant.

The supernatant was mixed with an equal volume of PC (phenol: chloroform=1:1) and centrifuged at room temperature and 12,000 rpm for 10 minutes, thereby obtaining a supernatant. The supernatant was mixed with an equal volume of chloroform and centrifuged at room temperature and 12,000 rpm for 10 minutes, thereby obtaining a supernatant. The obtained supernatant was sequentially mixed with 10% (v/v) of 3M sodium acetate and double volume of cold 95% ethanol, based on the total volume, and left at −20° C. for 1 hour. Subsequently, centrifugation was performed at 0° C. and 12,000 rpm for 10 minutes, and the precipitate was obtained by removing the supernatant. Then, 50 μl of Tris-EDTA (TE) buffer (pH 8.0) was added thereto to thereby dissolve the obtained precipitate. The extracted DNA was diluted 10 times, and a concentration was measured by measuring absorbance at $OD_{260}$.

Figure 2:
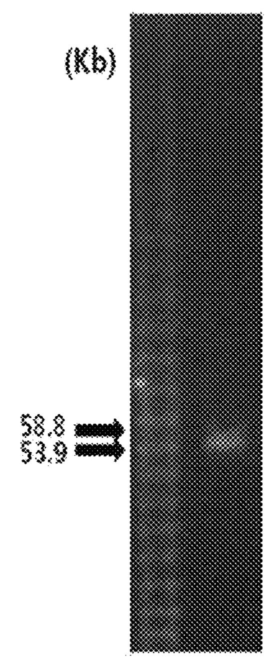
FIG. 2 shows a result of pulsed field gel electrophoresis (PFGE) of the novel bacteriophage ΦCJ22.

Next, 1 μg of DNA was loaded onto 1% pulse-field gel electrophoresis (PFGE) agarose gel, and electrophoresis was performed at room temperature for 20 hours using a BIO-RAD PFGE system program 7 (size range: 25-100 kb; switch time ramp: 0.4-2.0 seconds, linear shape; forward voltage: 180 V; reverse voltage: 120 V) (FIG. 2).

FIG. 2 is a pulsed field gel electrophoresis (PFGE) photograph of the genomic DNA of the bacteriophage ΦCJ22, and it may be confirmed that the genomic DNA of the bacteriophage ΦCJ22 has a size of about 56 kb.

EXAMPLE 4

Protein Pattern Analysis of ΦCJ22

15 μl of purified bacteriophage ΦCJ22 solution ($10^{10}$ pfu/ml titer) was mixed with 3 μl of a 5×SDS sample solution, and heated for 5 minutes. The total protein of the bacteriophage ΦCJ22 was expanded in 15% SDS-PAGE gel, and then the gel was stained at room temperature for 1 hour using a coomassie blue dye solution (FIG. 3).

Figure 3:
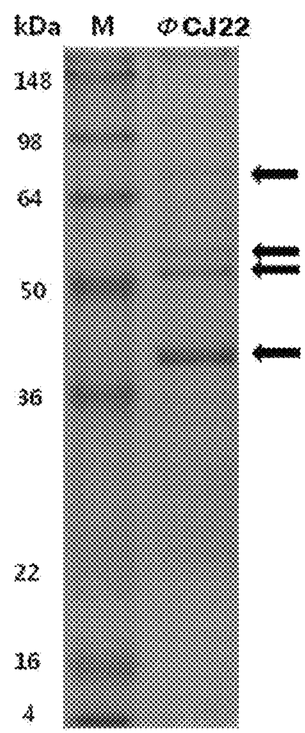
FIG. 3 shows a result of sodiumdodecylsulfate-polyacrylamide gel electrophoresis (SDS-PAGE) of the novel bacteriophage ΦCJ22.

FIG. 3 is an electrophoresis photograph showing a result of SDS-PAGE performed on the bacteriophage ΦCJ22, and main proteins having sizes of about 40 kDa, 51 kDa, 53 kDa, and 70 kDa were observed. In FIG. 3, M is a protein that becomes a standard for measuring a molecular weight.

EXAMPLE 5

Gene Sequence Analysis of ΦCJ22

In order to confirm genetic characteristics of the purified bacteriophage ΦCJ22, DNA of the bacteriophage ΦCJ22 was analyzed using a FLX titanium sequencer (Roche), which is a gene analysis apparatus. Genes was assembled at Macrogen INC. using GS and de novo assembler software (Roche). Sequence analysis of an open reading frame was performed using GeneMArk.hmm, Glimmer v3.02, and FGENESB software. Identification of the open reading frame was performed using BLASTP and InterProScan program.

The genome sequence of the bacteriophage had various similarities with that of the existing reported bacteriophage, but it was confirmed that a bacteriophage of which all of the fractions were completely (100%) equal to those of the bacteriophage of the present invention did not exist. Therefore, it may be confirmed that the bacteriophage was a newly isolated bacteriophage.

Homology analysis data of nucleic acid sequence between bacteriophage ΦCJ22 and other bacteriophages is shown in table 1.

TABLE 1

| Query | | Subject | | | | Identities | |
|---|---|---|---|---|---|---|---|
| Name | Length | Start | End | Description | E-Value | Match/Total | Pct. (%) |
| contig00001_orf00003 | 441 | 31 | 384 | putative protein [*Aquitex aeolicus* VF5] | 2E−10 | 53/152 | 34 |
| contig00001_orf00001 | 930 | 1 | 915 | domain protein, SNF2 Family, [*Bryantella formatexigens* DSM 14469] | 1E−51 | 101/315 | 32 |

TABLE 1-continued

| Query | | | | Subject | | Identities | |
|---|---|---|---|---|---|---|---|
| Name | Length | Start | End | Description | E-Value | Match/Total | Pct. (%) |
| contig00001_orf00011 | 324 | 37 | 306 | hypothetical protein ANACOL_03384 [*Anaerotruncus colihominis* DSM_17241] | 7E−07 | 38/91 | 41 |
| contig00001_orf00016 | 2868 | 2410 | 2859 | hypothetical protein ACS_2545 [*Clostridium perfringens* E str. JGS1987] | 7E−55 | 103/150 | 68 |
| contig00001_orf00013 | 218 | 1 | 207 | bacteriocin uviB homolog [*Clostridium perfringens* C str. JGS1495] | 3E−22 | 47/59 | 68 |
| contig00001_orf00012 | 1257 | 26 | 1254 | N-acetylfrazenoyl-L-alanine amidase domain, protein [*Clostridium perfringens* D str. JGS1721] | 1E−97 | 200/421 | 47 |
| contig00001_orf00017 | 588 | 25 | 573 | hypothetical protein HMPREF9630_00205 [*Eubaeteriaceae bacterium* CM2] | 6E−10 | 54/184 | 29 |
| contig00001_orf00010 | 1347 | 583 | 753 | hypothetical protein PCC7424_5514 [*Cyanothece* sp. PCC 7424] | 1E−05 | 31/57 | 54 |
| contig00001_orf00014 | 150 | 1 | 135 | hypothetical protein CLJ_B2512 [*Clostridium botulinum* Ba4 str. 657] | 9E−12 | 33/45 | 73 |
| contig00001_orf00021 | 987 | 1 | 980 | hypothetical protein 2016_scaffold57_00038 [unidentified phage] | 5E−41 | 109/328 | 33 |
| contig00001_orf00022 | 702 | 7 | 417 | ZkdP [*Bacillus* sp. JS] | 8E−10 | 53/139 | 38 |
| contig00001_orf00015 | 594 | 1 | 585 | conserved hypothetical protein [*Clostridium perfringens* E str. JGS1997] | 4E−25 | 72/198 | 36 |
| contig00001_orf00018 | 1059 | 25 | 1047 | putative base plate assembly protein: putative FBSX prophase protein [*Bacillus substils* subsp. *substils* str. 168] | 4E−52 | 119/341 | 34 |
| contig00001_orf00019 | 408 | 1 | 984 | Phage oxe element PBSX protein XkdS [*Clostidium inerinocelium* ATCC 27405] | 1E−14 | 48/126 | 37 |
| contig00001_orf00033 | 405 | 16 | 402 | hypothetical protein RUMOBE_O1056 [*Ruminococcus abeum* ATCC 29174] | 5E−10 | 44/120 | 33 |
| contig00001_orf00023 | 2562 | 25 | 1239 | phage tail tape measure protein TP901 family [*Herpetosiprion aurantiacus* DSM 789] | 2E−88 | 103/410 | 47 |
| contig00001_orf00031 | 584 | 43 | 522 | hypothetical protein B1NLASEDRAFT_3740 [*Bacillius* sp. 1NKA3E] | 1E−45 | 69/170 | 52 |
| contig00001_orf00037 | 885 | 19 | 879 | phage Mu protein F like family protein [*Geobacillus thermoglucosidans* TNO-09.020] | 2E−50 | 114/304 | 37 |
| contig00001_orf00026 | 432 | 10 | 420 | hypothetical protein RUMOBE_O1063 [*Ruminococcus obecim* ATCC 29174] | 8E−16 | 47/139 | 33 |
| contig00001_orf00030 | 435 | 1 | 339 | hypothetical protein putative PBSX [*Bacillus amyloliquefaciens* XH7] | 1E−07 | 37/116 | 31 |
| contig00001_orf00035 | 921 | 10 | 882 | conserved hypothetical protein [*Bacillus cereus* 0388108] | 4E−84 | 161/281 | 55 |
| contig00001_orf00038 | 1250 | 1 | 1080 | hypothetical protein RUMOBE_01052 [*Ruminococcus obeum* ATCC 29174] | 9E−63 | 184/395 | 38 |
| contig00001_orf00025 | 420 | 88 | 417 | hypothetical protein BSSC8_30350 [*Bacillus subtils* subsp. *subtilis* str. SC-8] | 3E−13 | 40/111 | 36 |
| contig00001_orf00032 | 363 | 13 | 336 | hypothetical protein B1N1A3EDRAFT_3747 [*Bacillus* sp. 1NLA3E] | 8E−13 | 45/108 | 41 |
| contig00001_orf00027 | 1332 | 1 | 1329 | Phage tail sheath protein [*Desultasparosmus youngtae* DSM_17734] | 1E−63 | 169/449 | 37 |

TABLE 1-continued

| Query | | | | Subject | | Identities | |
|---|---|---|---|---|---|---|---|
| Name | Length | Start | End | Description | E-Value | Match/Total | Pct. (%) |
| contig00001_orf00039 | 1455 | 100 | 1452 | hypothetical protein bthur0004_54930 [*Bacillus thuringensis* serovif sollo str. T04001] | 5E−80 | 194/407 | 41 |
| contig00001_orf00044 | 378 | 1 | 366 | dCMP deaminase putative [*Archaeoglobus fugidus* DSM 4504] | 5E−23 | 61/134 | 45 |
| contig00001_orf00038 | 1476 | 7 | 1458 | hypothetical protein RUMOBE_01050 [*Ruminococcus obeum* A7CC 29174] | 1E−108 | 221/499 | 44 |
| contig00001_orf00041 | 537 | 259 | 678 | phage terminase small subunit PBSX family [*Clostridium botulinum* Ba4 str. 657] | 2E−26 | 66/184 | 40 |
| contig00001_orf00050 | 584 | 91 | 558 | conserved hypothetical protein [*Clostridium botulinum* BKT015925] | 3E−05 | 42/161 | 26 |
| contig00001_orf00058 | 207 | 1 | 204 | hypothetical protein phl34O_gp33 [*Clostridium* phage phiCP34O] | 1E−12 | 32/56 | 47 |
| contig00001_orf00057 | 363 | 34 | 294 | putative phage related protein [*Seleriomunas ruminanium* subsp. *lactilytica* TAMB421] | 4E−09 | 34/87 | 39 |
| contig00001_orf00062 | 566 | 7 | 570 | thymidine kinase [*Clostridium butyricum* E4 str. BoNT E BL5262] | 2E−55 | 109/100 | 57 |
| contig00001_orf00059 | 594 | 37 | 537 | hypothetical protein CbC4_4068 [*Clostridium bacterium* BKT015925] | 5E−17 | 66/191 | 34 |
| contig00001_orf00065 | 1974 | 133 | 1566 | prenase [*Gordonia* phage GTE2] | 3E−36 | 137/494 | 27 |
| contig00001_orf00086 | 526 | 247 | 300 | hypothetical protein [*Pelotomaculum thermopropionicum* Sr] | 0.0003 | 17/36 | 44 |
| contig00001_orf00073 | 762 | 358 | 756 | thymidylate synthase [*Clostridium acetobulyacum* OSM 1734] | 8E−16 | 45/134 | 33 |
| contig00001_orf00074 | 183 | 16 | 100 | hypothetical protein ACS_1713 [*Clostridium perfringens* CPE str. F4909] | 6E−03 | 30/70 | 42 |
| contig00001_orf00080 | 864 | 46 | 702 | gp089 [Lactococcus phage KSY1] | 2E−06 | 57/220 | 25 |
| contig00001_orf00078 | 2442 | 226 | 2388 | DNA polymerase I [*Gordonia* phage GTE2] | 2E−97 | 256/756 | 35 |
| contig00001_orf00079 | 930 | 7 | 880 | hypothetical protein [*Gordonia* phage GTE2] | 2E−12 | 77/324 | 23 |
| contig00002_orf00001 | 366 | 40 | 321 | hypothetical protein DSSCB_18350 [*Bacillus subtills* subsp. *subtills* str. SC-8] | 2E−08 | 49/100 | 40 |
| contig00001_orf00082 | 345 | 22 | 282 | hypothetical protein FAEPRAM212_O159B [*Faecalibacterium prausnitzil* M21/2] | 3E−11 | 37/87 | 42 |

A partial genome sequence of bacteriophage ΦCJ22 is the same as SEQ ID No: 1. The genome sequence was determined by genetic analyzer.

EXAMPLE 6

Stability Test of ΦCJ22 Depending on pH

In order to confirm stability of the bacteriophage ΦCJ22 in a low pH environment, stability test was performed over a wide pH range (pH 4.0, 5.5, 6.4, 6.9, 7.4, 8.2, 9.0, and 9.8).

For test, various pH solutions (Sodium acetate buffer (pH 4.0, pH 5.5, and pH 6.4), Sodium phosphate buffer (pH 6.9 and pH 7.4), and Tris-HCl solution (pH 8.2, pH 9.0, and pH 9.8)) were prepared at a concentration of 0.2 M, respectively.

After 90 μl of each of the pH solutions was mixed with 10 μl of bacteriophage solution having a titer of $1.0\times10^9$ pfu/ml so that a concentration of each of pH solution became 1 M, each of the pH solutions was left at room temperature for 30 minutes, 1 hour, and 2 hours. Then, the reaction solution was diluted step by step, 10 μl of the diluted solution at each step was dropped and cultured at 30° C. for 18 hours by a soft agar overlay method, and the titer was measured through the presence or absence of lysis (FIG. 4).

Figure 4:
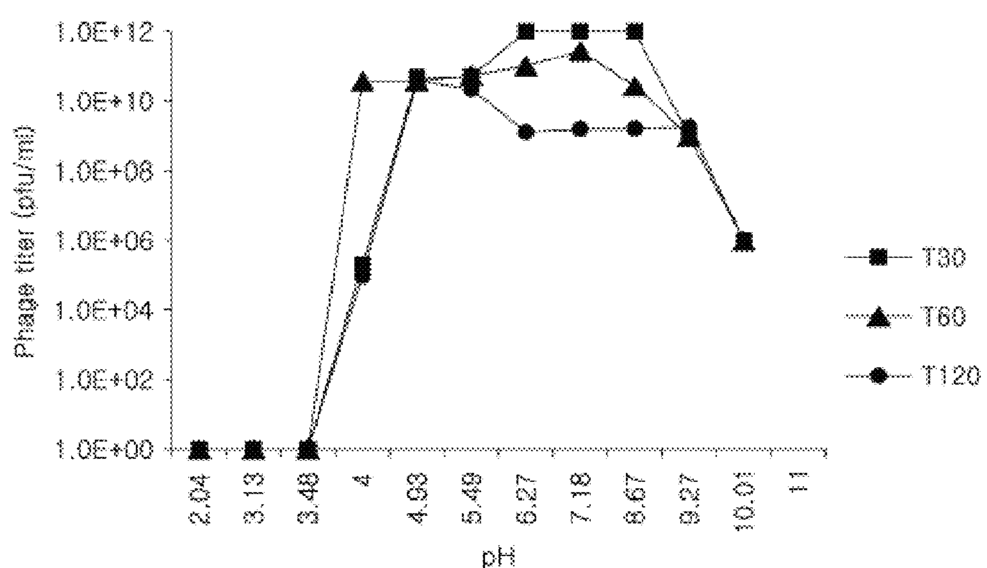
FIG. 4 is a graph showing a result of an acid resistance test of the novel bacteriophage ΦCJ22.

FIG. 4 shows a result of the acid resistance test of the bacteriophage ΦCJ22. As shown in FIG. 4, it may be confirmed that the bacteriophage ΦCJ22 did not lose its activity and was significantly stable in a pH range of 4.0 to 9.8 for up to 2 hours.

EXAMPLE 7

Stability Test of ΦCJ22 Depending on Temperature

A test for confirming stability against heat generated during a formulating process of the bacteriophage in the case of using the bacteriophage as a feed additive formulation among formulations of the bacteriophage was performed.

In detail, 200 μl of bacteriophage ΦCJ22 solution having a titer of $1.0\times10^8$ pfu/ml was left at 60° C. for 0, 10, 30, 60, and 120 minutes. Then, the solutions above were diluted step by step, 10 μl of each of the diluted solutions was dropped and cultured at 30° C. for 18 hours by a soft agar overlay method, and the titer was measured through the presence or absence of lysis (FIG. 5).

Figure 5:
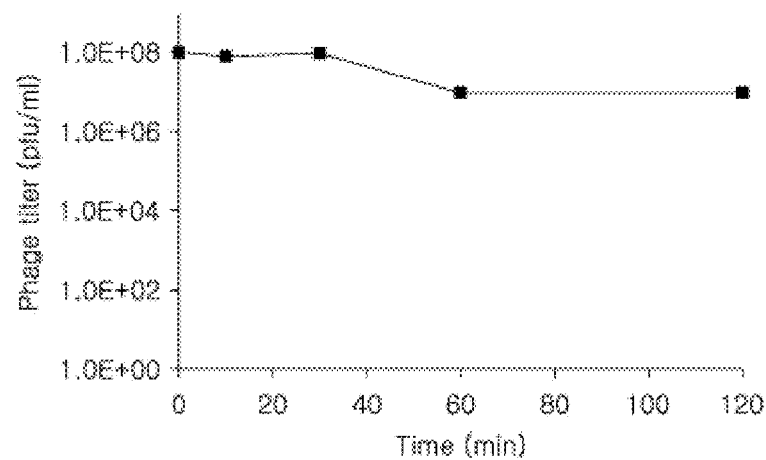
FIG. 5 is a graph showing a result of a heat resistance test of the novel bacteriophage ΦCJ22.

FIG. 5 shows a result of a heat resistance test of the bacteriophage ΦCJ22. As shown in FIG. 5, it may be appreciated that the activity was not significantly decreased until the bacteriophage ΦCJ22 was exposed at 60° C. for 2 hours.

EXAMPLE 8

Stability Test of ΦCJ22 Against Drying

A test for confirming stability against drying conditions generated during a formulating process of the bacteriophage in the case of using the bacteriophage as a feed additive formulation among formulations of the bacteriophage was performed.

In detail, 100 μl of bacteriophage solution having a titer of $1.0\times10^8$ pfu/ml was dried at 60° C. for 120 minutes using a speed-vacuum concentrator 5301 (Eppendorf). The pellet obtained after drying was put and resuspended in a SM solution at an amount equal to that of an initial solution at 4° C. for one day.

Figure 6:
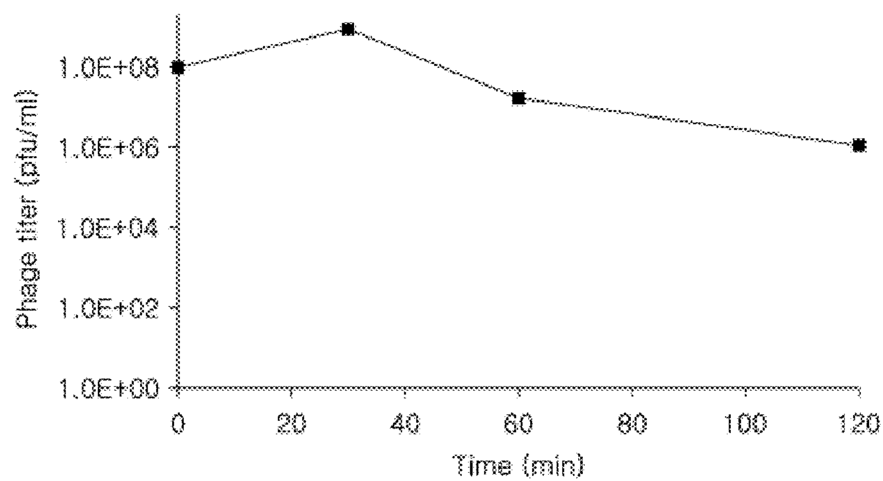
FIG. 6 is a graph showing a result of a drought resistance test of the novel bacteriophage ΦCJ22.

Then, the solutions above were diluted step by step, 10 μl of the diluted solution at each step was dropped and cultured at 30° C. for 18 hours by a soft agar overlay method, and the titer was measured through the presence or absence of lysis (FIG. 6).

FIG. 6 shows a result of a drought resistance test of the bacteriophage ΦCJ22. As shown in FIG. 6, it may be appreciated that the bacteriophage ΦCJ22 was decreased by about 2 log value after drying.

EXAMPLE 9

Infection Spectrum Test of ΦCJ22 with Respect to Wild-Type Strains of *Clostridium perfringens*

Whether or not the bacteriophage ΦCJ22 had a lytic activity was tested on 45 wild-type strains of *Clostridium perfringens* isolated by Animal and Plant Quarantine Agency and Kunkuk University other than *Clostridium perfringens* (BCCP 17-1) used in the experiment.

In detail, 10 μl of bacteriophage ΦCJ22 solution having a titer of $1.0\times10^{10}$ pfu/ml and mixed with 150 μl of a shake culture solution ($OD_{600}$=2) of each of the strains was dropped and cultured at 30° C. for 18 hours by a soft agar overlay method. Then, whether or not a plaque was formed was observed. As a result of the experiment, among 45 wild-type strains of *Clostridium perfringens*, 42 strains were infected, such that an infection ratio was about 93.3% and a lysis ratio was about 75.6%. The results were shown in Tables 2 and 3.

TABLE 2

| Origin of CP | CP strains | Infectivity |
|---|---|---|
| Kunkuk University | HLYS-1 | – |
| | HLYS-3 | ++ |
| | JSH-1 | + |
| | KCCM 40947$^T$ | +++ |
| | KJW-2 | +++ |
| | OYS-2 | – |
| | KCCM 12098 | ++ |

TABLE 3

| Origin of CP | CP strain | Infectivity | CP strain | Infectivity |
|---|---|---|---|---|
| Animal and Plant Quarantine Agency | CP-KJW-1 | +++ | BCCP43-1 | +/– |
| | CP-JSH-1 | +++ | BCCP44-3 | + |
| | CP-OYS-2 | +++ | BCCP47-2 | +++ |
| | CP-BC-1 | +++ | BCCP48-3 | +++ |
| | CP-BSW-4 | +++ | BCCP50-1-3 | +/– |
| | CP-HBM-2 | +++ | BCCP50-1-8 | +/– |
| | CP-HL | +++ | BCCP51-1-1 | +++ |
| | CP-KW-1 | +++ | BCCP51-1-5 | +++ |
| | CP-BS-1 | – | BCCP52-2-8 | +++ |
| | CP-HL-1 | +++ | BCCP53-2-3 | +++ |
| | CP-LJN-1 | +++ | BCCP54-3-8 | +++ |
| | BCCP17-1 | +++ | BCCP55-3-1 | +++ |
| | BCCP23-4 | +++ | SBCCP429-2 | +++ |
| | BCCP37-2 | +++ | SBCCP321 | +++ |
| | BCCP38-1 | +++ | SBCCP343 | +++ |
| | BCCP39-1 | +++ | SBCCP361 | +++ |
| | BCCP40-1 | +/– | ELCCP Suksan Kim | ++ |
| | BCCP41-3 | +++ | ELCCP6-1 intestines | +/– |
| | BCCP42-2 | +++ | ELCCP6-1 appendix | + |

The invention claimed is:

1. A method of suppressing or treating an infectious disease caused by *Clostridium perfringens*, comprising administering a bacteriophage ΦCJ22 (KCCM11364P) to animals except for humans.

2. The method according to claim 1, wherein the infectious disease is necrotic enteritis.

3. A method of suppressing or treating an infectious disease caused by *Clostridium perfringens*, comprising administering a composition to animals except for humans, the composition, comprising a pharmaceutical acceptable carrier and a bacteriophage ΦCJ22 (KCCM11364P) having a specific bactericidal activity against *Clostridium perfringens*.

4. A method of preparing an animal feed composition, the method comprising:

providing a bacteriophage composition comprising a bacteriophage ΦCJ22 (KCCM11364P); and mixing the composition with an animal feed base to provide the animal feed composition such that the bacteriophage is in an amount of 0.05 to 10 parts by weight based on 100 parts by weight of the animal feed composition.

5. A method of feeding, the method comprising:

prepararing the animal feed composition according to the method of claim 4; and feeding the animal feed composition as a feed to an animal.

6. A method of preparing a drinking water composition, the method comprising:

providing a bacteriophage composition comprising bacteriophage ΦCJ22 (KCCM11364P); and mixing the composition with drinking water to provide the drinking water composition such that the bacteriophage is in an amount of 0.0001 to 0.01 parts by weight based on 100 parts by weight of the drinking water composition.

7. A method of feeding, the method comprising:

prepring the drinking water composition according to the method of claim 6; and feeding the drinking water composition as a feed to an animal.

* * * * *

SEQUENCE LISTING

```
<160> NUMBER OF SEQ ID NOS: 1

<210> SEQ ID NO 1
<211> LENGTH: 52133
<212> TYPE: DNA
<213> ORGANISM: Artificial Sequence
<220> FEATURE:
<223> OTHER INFORMATION: a novel Clostridium perfringens specific
      bacteriophage KCCM11364P

<400> SEQUENCE: 1

ataaaattat gaactcaaat attctaggag ttaattggaa acagtttgaa gatgacttta     60

taatcaaagg aggttatatg aactatgaaa ttgtggggta taagaatgag gaaatattaa    120
```

```
agaaccttat gcaccagaat tgctatatag taagaataga agattgtatt gatttaccag    180
aacaacttcc tgatctgtat ttaacctgtg aattaaatag taaagccaga aaggcctata    240
atgaccttag aaaggaaatg atagcacaac tagatatagt acaggaaaac attcctagga    300
agcaattaaa ggccttatta aggtctaatg gtataccota tgagagtaat gagccctatg    360
aggatttatt cttaagggct aatatgttta tcaaccaatt aacagctgat cttactatta    420
cccaatattt gaggctacag cagatctcag gaggatttat tacaaacaat gtaggaaata    480
gtattaatat tgataaaggc aaattaggct tgttacagga ctatctagaa ggatataaaa    540
agcctgttgt tgtaatatgt aattttcttg aggaaataaa acttatacat gatacttta    600
aaaagaccca cagagtagaa tgcttaacag gatctactaa gaatagagct gagatcaata    660
aggattttca ggagggcaag attgacatat taatactaca aataagttca ggtagtgttg    720
gtctaaacct cttcagggcc tcaaggttaa tattctatag ttggaactat aaatatgatg    780
attatgtgca agctattgcc agaatcaaaa ggaatggtca aaaggagcct tggcaaataa    840
tacacttaat aactgagaat actattgatg agaaaatatt aaaatcaata cagcttaaaa    900
gggatagagc agaaaaactg ttgactattg ataagtaatg tggtaatata gaattgaggt    960
gataagtaat gagaaaagaa caacctagaa taagtaatca tactgaaata gctaaagctt   1020
taattgaggc tggtaaaact attaaagccc taaccaagat taaagtcaag gaggaaaaga   1080
aaaaacaaaa gggacttgaa aggttaagac tcctaaatga ggaaaagaag aaggagagag   1140
aattaatgaa agaatttaat cctaatgagc ccaagaagcc aagaaagaaa aaggacaaac   1200
ctataaagaa ggttgatctg aataaagttg aggccaaagg agattaccct actactccgg   1260
gaagtaatgc acccatggga acagttgatt taaaatcttt atgtgagtca ttaggattag   1320
atccaagtaa agccagagcc aagctaagaa agcaaggggt aaacaaaccc tataaatggt   1380
caggatctga acttgaggat attaagaaaa tgttaaaata aggggaggtt taaaaacctc   1440
ttctttttcg ttgacaatat ccacagtata tggtaatata aatattgtaa tcaaacaaaa   1500
aggagagaac tgaatatgaa agatcttgaa aaacttacaa gggaagaatt gattgaactt   1560
gtaaaggagt tatctattga ttggacagga gcctataata gaaactataa gattgacctt   1620
gatgagtatg agattgtata tattgatctt aatgatctaa aagagttcaa tgataaatta   1680
ggtcatctag aaggagatgt gtatatacaa tacactgtaa atcttattaa ggcccattta   1740
catcctgaga aggatatatt gattagatgg ggtggtgatg agtttgtagt tatcagtgat   1800
atagcttata atctgtgcaa taccttgaac atataccctg agttatcatg tggctatggt   1860
aaaggtaaaa ctattgaaga agctatagta caggccgact caatgatgta taagaataaa   1920
aaatctaaga agttaagata ctcaaaggag gattagttat tatgaggtta ttatggttaa   1980
aagagtattt ggatatatgc aatatcttgg gtattgagcc cacaatggaa gcttgtgcta   2040
ggtggggaaa gaataaaaaa ttatcagggt tttcattaac cccegtagga gcaactaaat   2100
agttgcttct ttttaaagcg atccgatacc tagcaacttt catgccaaaa agaaattcgg   2160
gattttcttt gacatagact ccagagtctg gtataataat cttgtaaaca aaattaattc   2220
aaaggagttg ttaattatga ataacaaaaa atttcaagaa actttagaac aattaaagga   2280
ggaactagaa atacaagggg tagaatttaa tgatgagaat gacttaatag ctgctgttga   2340
atacatcata gaatatgatt accacccaga acaatatgtg gaagatactt tatgtaacta   2400
ccctgaaatg ttcaaggatc tataaaacta aggaggtgta aaaacctcct tttttatttt   2460
```

-continued

```
ttcgaaaaaa tctggattta atcgttgaca ggatcgggac tatctagtat aataatattg   2520
taatcaaaat taattgaagg agatgttaac tatggaacta acaagatcag aaaaacttaa   2580
tgtaataaag ggaattgctc aaaaggctat ggataataaa atctatccac aatttagaaa   2640
agaactagat aaacaggtaa aatcctttgg actaagcaac aaagttaggg aaagtgaatt   2700
aggagactac ctttcttgct gcatggttgc ctatgaggag gttatcctaa aaatgaaaaa   2760
agcccattaa taggggtggc caaaaggcca tctatttttt tcgaaaaaaa tctccagaat   2820
ctcgttgaca tagtctgggc cctctggtat aataatattg taatcaatat taattaattc   2880
ttaggaggaa tgaaaaatga ctaaattaga aatgttaaat gagatagaaa aaataaataa   2940
ggtggttttt gaaaagaact tccaaaaaca attcttggat aaggtgatag aactactaca   3000
acaaatggga gtaactaaat attatgtatg taaatatcat aaaaaagctg agattgaaaa   3060
atatcttgat gcttgcatct gtgcaatata tgatatagga agaagggatg atctaggagg   3120
gtaaaacccc atcctttttt ttcttcgaag tttttcgttg acagatccag agttctctat   3180
tataattaaa tcataaatta actattggag gtaaacaaaa tgagagatat gatagaaaat   3240
caattagctg aatatgaagt aaaggagtta tacaatgagg ccacaatgat cttaggaaaa   3300
gcatttggtg taagtgctgt tgatctttat atagaatctg atgtggatgc taactactat   3360
ggtctatgcc atagatcagg taataaattt actgggatta caattaatct tttccctttc   3420
aggtttgcac aggaaggaga aaaagcttat gataagatca aaaaatttgg ctgggatatt   3480
aaggactgtg ttcttgaaac tatatgccat gaattggctc acttaactta ttggtcacat   3540
agtcctttac ataaaaaatt aactagtctt tattacaaca aagtacaaca ggctagaaag   3600
ggtgagaact cagctgtagc tcaaactaga agtgatatat acactttaaa agatctatgt   3660
gaattgatag aactagatcc aaggaaagcc agaagtatat taagaaagaa caatattgag   3720
aaaccaggta aacaatggga atgggagcaa ggtatgccta aagatatata tgatctatta   3780
ataaacctaa aagttagggg aagaaaataa tttcttctcc ctcttttttc gttgacatat   3840
ctcgagagtg ctggtataat tatattaaca aataacttag gaggtaaatc acatgataga   3900
tatatattac agtattcaag tagaagctga aaatttcttt ggttgtcaaa aggaagatgg   3960
aagctgggta gcaacggggg catttagtat accagttaac agcataacct ttgaagaggc   4020
tgacaaatta tctaatgagg ctatagatgg atggctaaag gaatatgagg ttactagggt   4080
aattagtaga agatcacatt cacaggttaa gctagattgg tataacagtt atatcaagga   4140
tgacccatta aagggtgata taattaatat ggtatatcct gatctttctg ataaggctaa   4200
aattaaatat ggttttggta agatatgggc tagcactatg tcaaaggttg ctaagaaagg   4260
tttacttaaa acttgcccta gatgtggagg cactggccat tactcaagaa cctcagatgg   4320
taacactact tgctttaaat gtaacggctt taaatatgtg ataccaacta agatctcaaa   4380
gaaattttat aaatctgtgg agaaaacctt tgacatctct ggcaataact cttataataa   4440
acttgtaaac aaaaacaaag aggagatgtt aaatatgaac ttaactgcaa tggaaataaa   4500
gatattaaat gctatgagaa agaatgaatt tgatgacgga ctagatgttg actgtgtatg   4560
ggtattctca gtaatagaaa actcaggtat agaaggaact aaggctagag gtgtgatctc   4620
atcacttgtt aaaaagggtt tagtatttgc tgatggagag gtaataggtt acacagaaga   4680
aggaagaagg gtctttgata atgctgatgg agaagaatgt aactggggag gtccaaaatt   4740
attaaaagaa atccctgaca aaccagagga aatctcttat aatgaaaatg tagataaaac   4800
aaataagaaa gaagaggtaa atgatatgaa agatttaaat actatgaaag ctgttgaaat   4860
```

```
taaagaatta gcaaaggagt taaaagttaa aaactggtgg actatgaaaa aggctgatct   4920
aatagctgct atccaacaaa tccaacaacc acaagaagaa aaagttgaag aggtacaaca   4980
accagctgaa cctgaagaaa aggctgaaca aactaaaatt actcttgatc taacagatgt   5040
taaggaacca gagaaaaaag ctgaaccaaa aactaaggaa ggtaagttca cattaaaaat   5100
gatacttgaa gaattaaata tgaatggtaa aaaggcaaga agaatcttaa gaaacaaaga   5160
agttgtaaaa ccaggaaagc aatgggaatg ggataatgaa gaagaattta aaaaggttaa   5220
ggacctactt tctaaataaa gtaggcccaa cctctatccc ctattgattt acaggaggat   5280
ctgattttct cttatccatt aactgcttcc atacttgatt accaaaggaa gctacagctg   5340
cacatattaa accctgtata aagccattca aaaaggtctt ggctgtaaaa cctaattcta   5400
attgaattgc catatataag attgataatg atatactgaa tatcaaaagt attaatggta   5460
tagaccaatc tggtatataa ggcttagcct tgataaacag acctaaacag taacatgata   5520
caatgattat taaaagctgt ggatcaatgt aattgaatat taagtttact aaattttctt   5580
ccatgataaa taccccctaa attatctcta catattttga acttacataa ccttgcttct   5640
taccgtggct agtattatat tctatatgat accaaccatt cttacttccc aatatagtaa   5700
ctctctcatt actaaatact gagcctatta tattaccatt cacatcatct cttacattaa   5760
gagaagtgtt aactttaact attccttgtt taacatcctc atagaatttc tggctttgct   5820
caccctcgta gcgaacgtat ccatcagatg gagtaccatc ctttctataa aatgttattc   5880
ttaaccagcc attagttcta tacattgggc tagccttttg accaggctgt agttcttcat   5940
tatgatcttt gatgttaacg tcttcagggt tccaccacac ataagttact ccattgtcat   6000
tttgatattt catgtggtag tcaaaactta atctactata atgttttata tctatatagg   6060
catgataatt gctgttcttt ccagggtata taacttcaat atattttcta gaaggatata   6120
tcccaaggac aaataaatta tctagactat caatatatct acctggaatt ggtttgcaat   6180
cctcatctag gacttctatt gaacctttcc ccaccaaagt ggcattagtt cttgtttctg   6240
aactttcata aaatccctta ggggcctcag gtaagcttgg ggtattatca taatcccctg   6300
agccagatcc ttcttgacca gttagtcctt tacatatagc agcagctata gcactaggat   6360
ttaataaatt acaatccttc tgacttgata caaagccaca ttcaactaat atagccggtg   6420
cattagtata tttaagtacc gctaggtcat aacctaaata ttctctagca actcttatac   6480
ctctgttata atatccaagc ttagcaagtt caactaatac tctcttagcc atttgttcag   6540
cttctccacc tctagcatga attagtacct caacaccatg agctgatgga tccttactag   6600
aatttaaatg taatgataca aaaccatcca ctccagcatt attagcagta ttatatctat   6660
gtgctaaact agcatctaga gaaggggcag aatcagtagt acaattaacc accctatcac   6720
caacagactc taaatcgctg attagagctt tacctatttt tctatcctca atttgctcag   6780
ttactatacc tgaagcccca gtatctgctc cggataatgt gtgccccata tcaattcccc   6840
ataatttact cataaaaata catctccttt aaatattata gtgttttatt aggcctgaga   6900
ggctcgctac agcattttaa ccacctcctt aatatatttt cttatataaa acctaacagg   6960
tcttaaatga cctgctaggc ttataattta acctttgtta ctaaataggt gatcttttat   7020
agtatctaca tcttccttta tatcctcaac tacgttgaat ttatcaacta gcttatctat   7080
cacttgattt aatttattct ctctttctct agcctctttt ctagtgtcat ataatagcca   7140
tacaaataga ctacaaaaga taccttggct aagaacttga gttagtagtt ctttttccat   7200
```

```
agattacacc ctttcattaa agtcttcacc acatattctt ttgtagtcct ctggtgtaat   7260
ttctccttct ggattagaag agcattttac tgcctgatgt aatttgtcct tacctattgc   7320
tccaattcta taagccattt cccagaaatt cataatctct acctccttat ttattcatca   7380
atttaatttt tatatcagct agttcttgtg ttagtacttt cattatggct ttggtttgca   7440
ttagctctaa tttagtatta gcaagagcct gagcttgata actaactaat ttattaatat   7500
ctaggggatt aggatctata gcctcatagg aagtaaatag gtccttatcc tttatgctat   7560
ataagtctga tcttttctta tttatatcaa acttggtagg ttctcctttt atgtggtcaa   7620
ataaacttac agtcatttgt ataaccggaa ggttatctag gtcaataacc tcagtgttat   7680
ccacaaaggc taaatgccct tgtgaattat gaggtatatg gagacatata atatcttcga   7740
tattatttaa tatctcacta ccctctctgt agtatagtgg ctctggtcta ttaattaggt   7800
ctaatatttt agtaacttct tcatggtctt tatctataaa tggttttaca tcttctgagt   7860
cttctgcctg atttatcagc atttcttttt catcatcata gaatataagg tctataacct   7920
tattagtttc cacagaataa ttaaatccta ctattctcat gttttatcaa ctcctttact   7980
cagtagctaa gtaggttagt attatttgag ttggtttacc agctaccatt tgataacatc   8040
caccatttag gtatgagtta gtccaatggt caatagtaca ataaccagag gtattattgg   8100
aagcgtcatt atagttatgt gatactagag atattggtaa tacccaactc caagccttag   8160
ggaaatgtat agtatagctt acacctccac ctgagttagc atagcctgtc ttaactattt   8220
gacgaactaa ccttacacct ccacccaagt ggaataccct agtactgtct ccattatccc   8280
aatagtctcc tttagctaca gatttattag ctacctggag gtcttgaaca ttctcagtgg   8340
ctagtattct accctcctgt ttataccaaa atcttccgtc ttctggacca ccataccagt   8400
catttattct catatatttt ctagccccta ggttttcagc tgatagagcc ttatccacat   8460
ctagggatcc ctctccagcg gttatcctca tatcaaaatc tttattactg ccttttaggt   8520
ggaagtctat aatatgccct acttccataa ccccatcatt accaatatta ggtacccctt   8580
gagttccttt actagagtca tatataccca tattagctag cttgttactg ttggcagctg   8640
tagcagtttt acctaagtaa gcattatcat ggttatggtt agaagaggct gctcctatct   8700
cagagggagt gggtttatta ttttgatgat aaattaaact cccactataa gctaatacac   8760
catcatccct taactgtaaa aatttattag actttttatt ttggaaatat acatctgttc   8820
cccctactcc acataataaa gctctcatat tatcatccct aagactagct aaggtagcta   8880
ctacatttac atttactaat tgatccactg taagtttgcc ttcaataacc ccgtcaccct   8940
ccttagctat agcccctatt tcttgaggtg taggcttatt atcttcatga tagatcttct   9000
tattgttctt attaacaata tctaaagagt ctatctttac aggccttcca gcatacccta   9060
tatggacttt attatctgca tctatataga tcacatagtc atcactgcct tctttagttc   9120
tacagctaaa tccatagttg tgcgccccta taaatttctg acctggcctc ataattagat   9180
gacctgataa ttctccaccc gtagtaggta gggcccctat ttcttgggga gttggtttgt   9240
tttgtttact atatatttca gcccaattcg tccatccagt accctccatg tttgtagctg   9300
ttctagtaaa aactcctcca ccatctgcaa agaacattgg agaagcccag tgtcctgtat   9360
tccaggataa aacaatcaat ctcccatctg ctagagttgg ggcatttttt tcaatagaat   9420
ttctaactgt agaataaata cccccctctg taatggtgtt tagatctaca ccctctagtc   9480
ttttggctgt tttatcccag gcccctatat cagcgggagt aggtctgtta ttctcatcat   9540
aaacctttac ccaatcagac caggtgttcc cattataaaa ccctctagta taggtaatac   9600
```

```
ccttaccatt tggaggtatt gttttaaacc tctgtactac ccaatcgggg ctatacctaa   9660
taacttccat aattgatata ccctgagaag gagcatttgc catgttttta tacccactat   9720
atattccagg tattttaata ttatttaagt cagtatcatt catgtctaaa tatgcagaat   9780
aagcaccaat ttcttcagga gtaggcttat tggcactatc ataggcctta tgccactttc   9840
cccatgtgtt actctcatat acatagttcc taatatatcg agtgatagta tcgctaggat   9900
atagattaat aaactcctgt tgaaacctat tcttaccatc acctaaacct gtatttctaa   9960
gaataaatac cctagcactc ccctgggcca gtgttccctc gggtgtattt ttaaaatcac  10020
cattccccgt atcaaaggag cagaaggagt ttcctgcttt aaaggaatta caatccctat  10080
ccacaggtac atcgaccttt tggatcacat ccactttggc agctttttgg tttacttggt  10140
tttgtaaact agtgtctttc tcaaataata gatctaatct ttttagcaca tcctcagggg  10200
ctaggttata gtcaggtact acattacctc tagctaataa ggtatttaat acctttaatg  10260
atgtgcttga ggttgcaccc tgtaccacaa attgtatttt agtatccgta gctccagagg  10320
gaatactaaa cttatgagtt tttaatttgt acccattact ctgtggtgta ctaccttgct  10380
ttacaatact cttatattgt tgacctccac tagtagtgta agccagttta atctcatagc  10440
tggtaaaact accctcaata tcttctaaga aggctaatac gtaatcacta tttggttcta  10500
taggcagagt tttaatctca agagtttgtg gacctgttga cataccagac catttaaaac  10560
ctcgtctctt agttggagta tctgtaatag gtgtgatatt accaggacca gtataagact  10620
cagagttgta ccactcaagc ctattaatag taccaaccct taaagcatct agcctatcct  10680
cattagactt agacttcttt tctacctcag tcattttctg tttatgttcg gcagcgaagt  10740
tctcaatgtt ttcattgtcc ttgttaaaat cattcatttt tggcttatct gttaactccc  10800
acttatttaa acctagagta ggagttttac cagtacttgg cattttgcat acctccttta  10860
ttcagttata gcatattctt cccatttttc ccaggtaagg tctagactgt cccacttgct  10920
ccacatataa tcatacctat cgaacatctc ccaagtaata taaagtaata taatttgata  10980
tattaaatga gcaggcattc tttctctgaa tactctttct agagccttta ggttaggtgg  11040
taccccctggt aggtcagtaa agctaatttt gatcttactc tcttcagcta tgaactctac  11100
ctttaccttt ccacccgtat aggccttagt aagatttttg atagatgtac tattaaactt  11160
tttccaagca gatagaacta ctgtaataat agctcttttc tcttggtcag ttggtgggta  11220
atcaaagtat ttatataatt caagatcagt gaaaaatctt tctagacctt ccttaggagt  11280
ggtcttggga tccacatagt cttgtaattc ctgtccctta gtatatagct tctgaagttc  11340
agtagccata atagtgttta ctaagttatc agcctctttt atattatcat aaaattcagg  11400
aacgtacaat agtaattctt tttgaacctg ttctagacta tacataagtt accaccacct  11460
cagtaatggt tggtatttga ttagcaggaa tagttaaaga ttgactactc ccattaagtg  11520
taatggttgt ataatcttct actccctcaa tatttaaaag catagcccct attctattta  11580
tagataggct agtaatttta aatacttgac tatttagaaa ttcttctagt tctttcttga  11640
agtttaattt tatttgttct tctgtaactg aactcaattt cttaacttga gctcttacag  11700
tgatattaaa ggtttgagct gactcaacag taaaaacaca tcctatagga gctttacctt  11760
cacctaaacc tttcttgcct ggatccatgt attcttgaac tttattaact aattcaggat  11820
tggcaggctt attctcaact gtggttataa tacctttagc agtatttata ccattccaac  11880
agggaagaac cacagcttta cctactccag ctacactttt acaccaatca gttaactgtt  11940
```

```
gaacatttcc atctcccgat ggttgtatag tggctttggt agctctttct cttaactcat  12000
catctgtctc ttgatctcta ccaataacaa gtatatctcc catagtagca ctcttaagtt  12060
ctgctatagc attgataggg attagatgtg tacctgttga taccttattg ggtcctgaac  12120
ctaaggtctc acattcaata atattaggct ctatcacttg ccagaaataa tctcctcctt  12180
ggaatcttga accaacatcg ggttcatagc caacaaattt agctgacctt ctacacttag  12240
ttggaattat tctggatatc cctacattgg cagctctctc atctaagaac ttacctgtag  12300
cagtacttag aaatactgag tctaatattt gattaacatt aacagcataa aactcagcta  12360
gcttaacagc aaaaaccata gccatatcat aggtgaaact tccagttcta gtgtcaatat  12420
catcagggga taggcctatc atttcttcta ataattcttt atgtgttcgg gagaataaat  12480
cttcagaaaa tcccattata tcaccccttc cagttttgta tctccatata tggtatttat  12540
ccatacttca atatatacat tcttaccttg cacattatac tttagatcag ttactttagt  12600
cactctatca tcttctaaga gacattcagg gatagcccta ttaatctcca tttcaagaag  12660
ttcaggagtt actagagagt cattaatcaa agctctaata tcacaaccat aagaagtatc  12720
ttgataaatc atataggcat ttttaggagt tattaatctt ttatataaag attgttttaa  12780
ggcctcaaga ccatccacat tatcataaat cctattaaga tctagatcca gtttgtaggt  12840
cttggtattc tccattgttt tctcatcaac tataagggta tctttaaagc cattaggtag  12900
cattatatca acctcctaag atccctaaca taaaatatct ttgtccatca tcatagggca  12960
taaggtaaac agtatcaccc tcactaatag actcaatatg ttttggaaca tctataaatat  13020
ttccagatag tactaatttc ctattgtgaa gacactcaca ttttataggg ctggtactaa  13080
gtactttagc tctataaata tttagagggg tagacatatt actatatact tgttttacac  13140
aatctaataa attattagcc attaaatatc accctcctca gtacatttaa gttttaagtt  13200
catggtgtag tcagtatcga atttatgagt atcagactca atgtagaaag ccttattaat  13260
ttttaaatgt ggtatactaa ctacaatggc tttaccacta atacagtcag gtacacctat  13320
aacagttata gaaatatccg ttttaggtct cttacctgtt tctagcttta ttctagcctt  13380
ctcatttaat tgggcttggt ttagttcatc actgatagta tcgtataatt gaaatacacc  13440
atatttcttt tggctgctat catctttagc agaggcaaat aaagtaatct cgggatcatc  13500
tttaccctta ccctgtttat atttacatac tagctttacc tggttgacaa tactatcaaa  13560
gtttctactt cttgaaaaag ttccaatatt tttaccatat tcgaatttcc acaattcttt  13620
agtggttctt cggtttataa aatcaaactt acctgtaata gaattataat aaatataaaa  13680
ctgttctcca gtttgttcat aaacctcttt tattaccttc ttcataatat catagggagt  13740
ttgtttctca catactaaac tagagaaagt atatccagtt ttagctacta ctccaggggc  13800
aaccccaaag gctttacata atgactcaaa tatagcttcg ccagtttgat tttcgaatac  13860
aaaactatct ttattattag cccaataaat catagggtca taagctttaa ctttaagtaa  13920
atgctttttc tcattatctg agatattcat aataatacca ttaaagatat tcttaccctc  13980
atggactagt actacctgat ctccatcata aattggatgt atatcttgag cattatattg  14040
gaatgatagg gtacgagggg cagatgaaga agaccctgcc caactcttac cactggaggt  14100
atttgtaata tcaaaggatt tatctccttg taccacaatt aattgcatat tataacctcc  14160
ttatataatc accagaactc caaccttcct tatatcctga accattatct aatttatact  14220
ttacataatg ccatccattt tgagacctta atactgtaaa gtgttcatta ggccatatct  14280
tacccttagt aggattattg ataccaggtc cagttcttac ccatagccat gagtaaacat  14340
```

```
tagtagtagt agctgcccaa ggttgagtac ctccagaaga actaccacct gtattaccac  14400
tataggctag tttaggtttt ggaattgtga aactaactga tttaacctca ggcttcttat  14460
actcagttag ttttattttt acttgaagag taccaatatc tccacctttc tcagtatatg  14520
agatattatc aatagtaact aataggttaa tatcagtact agtaatagta aatcttactg  14580
gatctttacc catttcaata agtttagcat aacttactcg ggggtctgca atatcagtat  14640
actcacatcc atcgtagtat gagcttggta actcaaaatt aaaagaaaaa gattttagct  14700
tagggtctcc tatgaaagag agttccccta agccttcaat ggaaactgta ctattatctc  14760
tactatcaga gatatttata tcagtgggat ttactggtaa cctaaaccta gtatctccct  14820
gtattaacca gaattgatat ttactatgca aggtccagat cacctccctc gaacatttcc  14880
tgatttaaca tttccacaat aaatctgtat actctcatta attcactttc tgagattgtt  14940
ccatcttcag cctgtactgt gaaattaaat gagttgttaa tgttcataac tttagatcca  15000
tcatcacttc ctgctccaga ttgtcttagt aaatcctgag ttttatctgc aggtaatact  15060
tgagagcctc taggcatttt tgagaatgta ggacccataa ctaattcggg accagcttca  15120
ccaaccatgg cagctttatc agtgaagaaa tcagtacctt cagcaagcat tggtatctgt  15180
ggaatattga tacctttacc tcctatgatt ggaacccagt ctggtatctt aatagtatta  15240
agagcaccaa ttaatccatt gattaaactg attattccgt ttataggtcc tttagcaaga  15300
gctagcatac cattgaatac tccaccgaat atattcttaa ctccctccca agctttagac  15360
cagttacctg taaatactcc ggctataaat gcaattatac cacttagggt ttgcattaaa  15420
gcttgaagaa tatttgagat attttgtacg gctccattta cagccgcagc aatcattggc  15480
caaacagcat taaatactgc tcctaaagca taaagtatag gagttagcat atccacaagt  15540
ccttggaata tcataccaaa actttctata gcagattgta tatatggaac tacactctca  15600
gcaaagctta agaacattgg taatagtgta ttattccacc aatcagctaa tccttgtaag  15660
attggcatta agatgttacc tattacttcc acaacttgag aaattgcagg agctatataa  15720
gtagcaaagg cctcagctaa agaagtagca attggcatga aaacattagt tatcaattcc  15780
ccaagagctg taaaagtagc agagaacata gaacctaata cttctaatat aggacctaac  15840
acttccaata cagtttgcca tacttgagta aatccctgaa cataaaggac tactaagtct  15900
atggctggaa ttaggttatt cataaatata gaagctaaag ttccaaacat atcaagaagt  15960
acttgaccta taggagctaa tactcccatg ataggctcag ctaaaccact aaaggcttct  16020
tgtatattat tgttagcctc tgataaataa tctggtagac ctactaagat ctccccaaaa  16080
ttattatata tgtcttctcc aagactccat atcttctcat taatttgatc tgccacatca  16140
gcaggtaaga acttatatag tatatcgttg gttagatcta taaaaggttg catagcatcc  16200
ccaaactccc aaccattcat gatgtaatat atagtctctc ctaaaccttg gaaagcagaa  16260
acaaccattg agaatatagg tcctagtttt tcaaagcctt cttgtataaa tgtgatacca  16320
tttaggacag cattagctat aacctcaacg gcaggggcta gggcatctcc cacatctaac  16380
ataactacag cagctttgga ttttattctc tccatggttc tattaaagcc cttatccatt  16440
ttttcatatg cagcttcagt ggccccagca ctattcttca tctcattaag agcattagta  16500
aaggcctcag taccttcacc agtcaaggct agtgcagctg aaccagcttc tacagaacca  16560
aagaggtcat tgatacccag attacttttc tgagcgtgtt tttctaacat ctgaagggcc  16620
tcttggatat tacctccacc tttaatgaag tctttgaaac ccttaccagc tatttcccgg  16680
```

```
aagaccttat cagtcttggt tcccgattta gatagctcat ctatagcagc tcttatctta  16740

gtggtagcta cagatgttgg aaccccctga gctgttaatg cagctataga ggcagatact  16800

tcttcaaagg ataccccagc agctgaggct gaaggtagca cattgaatag ggattgtgat  16860

agttgctcaa agttagtctt accaagtctt actgtagtaa acataaggtc tgaggccctt  16920

tgaacatcca tattcttagc tccatatgag ttaataacag tagttagtcc atcaaccgca  16980

gtttctattg atgtgatacc acctatagaa gctttaccag ctgtttctaa gaaactaaaa  17040

acgttatcct ctggaactga tgaggatatg gcttgataga gagcaggtac tactttatca  17100

ggcaatatcc ctatatcaga acttaacttt tttacctggc cggacatctt atcaaaggtc  17160

tcttgagtag agttaggtaa tagggtcata acctcattta acccttgctc aaaatcccca  17220

aaggctttaa tactgtcctt agtaaaatcc cagacagcct tagctgagaa tactccagca  17280

gccactccac caattttggc aagagtaccc atgaaggaat taccactatc agccatctgg  17340

ttaaatgcac cagagatctt atcttgggca gagaatatgg cagtaaatgc agcttgactt  17400

gccattatat ccctccttta tgattaagag cctttcttta acttatccct agctttctta  17460

tcttcttcta aagccagttc acatgaagct ataagaaagg ctttcctatt gggagatagt  17520

ttatcaaatt cccagggtag tatattatgc ttctggaata acacatgagc ccaaaatgca  17580

ctagtgtcgg cctttattag ttttttgctt ctttgattag atcatcctta ttatcgccta  17640

atccatttat gtccataacc tcactagtta ttctagtgaa atctcctggt aagcttagta  17700

catccataag taaatctact ggatccacaa acttagtaga ctctaaccat tttggatctt  17760

taaagtcagg gaatactatt gtttctagta tcatttccct agtagctctt ctttggtctg  17820

ttattgagtt agttatacct ttgtttctgg taattactgt atttctcttt tggatatcct  17880

ccatttgctt agtagtgatt ggctttaata tccaaggtat aggttggccc gctaattcat  17940

gaccctcagg gaaactaaat ctagctaccc cctcaacttc aatttcgggt gattgtttac  18000

ccttatcatt ttccatgaaa aattccatac taaattttga cataataatc tacctccaca  18060

atattcttaa tcttttataa atatcttact tctgaagctg agaatgatat ttcttcttga  18120

atttcttctc cctcagcatc tagtccaatt agtggtaaat ctccttctaa ttgtactcct  18180

agtaattgta ctctgtcctc accataattc ttaacatagt cagaatctgg atcatcacat  18240

acagcttgta tatccatctt agggaatata ccagtcttta agtattcttt aatagcttct  18300

cttatcattg gagtagcttt gaattgagtt atagttccag ttatatcata acctataact  18360

tttgaggtta atcctttctg acccataacc cttttcttag tcacctcagg agtaaataga  18420

gcttctaatt ttattaagct agttacttgc ttacctgata caaaagctct accctctcta  18480

gcagacattc tattaacttc actcatgggc tatacctcct taattattct taacagttac  18540

aaagtatttc ttgaaagttc ttacaggttg tgtaagtata gtagcataca tagtctttcc  18600

tttactagct tcttcatcta ccactacatc agagtcaggg tccacattct ttaatgctcc  18660

ttgagcttgt agtgtagtta atagacttat tagtctatcc tgagctagtt ttataccatc  18720

tttgtggtta gggaaaacat taggaactaa tatttgagat cctagatcta taacagcatc  18780

taatacagcc acaactttat tatctgtaaa gctttcatcc cattcttctg taaaagtatg  18840

gtgtgtattt atatcttcct caactactac ctttactctt tcagaatttg agtcagtttg  18900

agttgagaat ataaattgac ctgtttttaa tccatcaact atttgagagt gttttagtct  18960

tggattagca tctactgccc caggatatgc tttataagta aggtcctcag tatatccagc  19020

tgcagctcta gccccagcta cccatgcagt tgcttgagaa gcggttaact tagtgcctcc  19080
```

```
atctaataca accccatttt taacattgat gatatatggg taatcacaag tagcaaagtc  19140
agaagtaact gccacaatgt tcttaccaac ttcatctctg aagtatttaa gttttgataa  19200
tagagcagtg tgtaattcac tctcagtaaa tgggaaggcc atagttttaa agttgtataa  19260
ctcacagtta tctaagaagt tgataacatc agagttattc atctgagtag aagtaccagt  19320
actaaactca gtcttagcag tctcatctat agaaccactt ccacttactg taaaccattg  19380
agacttaact gttgatattt cagttactcc tgtagcctca aatattttag acccttcaag  19440
atataataat atatcctttc ctccaagagg attagtctta atagttagag ataatttatt  19500
acctctttct ccagctttag tagctgtaaa tgttagagac cctactacag ctttggcttt  19560
agttccacct gttaggttat atactaaaac agttgcagct tcttttaaag cctctttaac  19620
tagtaacaca gtagggtgag ttatgtcata cccaagttga tataatgctt ctaggccacc  19680
ttcattggtt accttgataa catctccagc attaccccac ttaagttgta atggtaagat  19740
cataactcct agattattaa gcttaggctc attaagtcca ccacttacaa atctagtata  19800
cataccaggt cttactttat tttgtcctgg aataaaagtt cctcctgcca tctattttac  19860
ctccttcttt agccagtctt ttataatctg actagtttgt tttattgtta actcttcatc  19920
aggtggaaga gattgaactg cagcgttgaa gacaaactcc tcaacctgga aaagttgttg  19980
acaatgggct cttaattgag gtatggaaaa tttttgtact ttcactattt taccccccttt  20040
gttatctcaa aattttcgaa gtaagttgga tctttataaa gactaaccac aatatcatag  20100
tttatctcta catgagaatc ttcttcagtt tcaccttcaa atacttccac attctttatt  20160
ttgagatttt tgttggtctt actaccatcc ctattaagta taggaatttt tctatttctc  20220
aagtatatgg cattagctat attctgagca atttcaagag agtctttagg ttcaaatacc  20280
ttaactctta gggtattctc agtcctataa ctacaaagag tatcattctg aggattaaat  20340
accttcttga aatataatga gggatacttg aatttttcag gtattcgctc aaaatagagg  20400
gtagtaattc cagttagatc agatatgaat ttagcaatac tccctatatc tgctgtcatt  20460
aataactacc ccctaaaact tcggctaacc aatcttctaa ttttctttgg aaagcctgtt  20520
caaatatttt ttcatatatc tttactgcat tgtcccaata aggtttacct ggtactttct  20580
tttgtcttag taccatacca gtcttagctc ctggttgata aataaactta tcccctgacc  20640
atatgccagg aacgaatcta aatgattgtc cttgtggatt agtgtagtga ccatcgttta  20700
cccacttagc atattttagg ttagtaccaa cttctaaagt tagtcctcca tcactactta  20760
cccatatacc attcttacct cccttttgaa aggagttaag taataatcta gtatctacta  20820
cttgtagtct aattatttca tcttgaacca catcaaggaa gtctatccct gcagcttcaa  20880
accatactgc taattgcttt ttgaaatcac tattagcggc atctcttagc ttctttataa  20940
acctttctat ttgtttagca tctatttcta tgcccccaga atttgaagcc ataactacct  21000
aaaatcctta gcctctatac caaccttaat ttttagaccc cttatatccc taggagcttt  21060
agctatatat gtgataccag tctcaaggtc cacaatttta tcattttgtc taacatcagt  21120
tccaatagca aaatctactg agtactcctg ggtaatctta aacctaggtt ctttgtactc  21180
aagtttttct agagttcctg atttaaaatg acagggtacc tcagtcatgt ctggctcatc  21240
aggataacta aagctagggg tatgggctag gccatatccg ggatcttcag gatcttctaa  21300
taggtggtat atattacatc tatgatttaa gagcttgtta tatgaatttc taatcatact  21360
acagtaccct taatctcata gtagttgttc tgatagatgg actatcatct tctaagaaag  21420
```

```
gtttaatcag aggcataata tcaggctcta taacagcctt atcagttctt cttgtatatg  21480
agtagtcatc ataggtctcg gattgaatat cagccttgct aatgaccaag gattgtagtc  21540
cataatactc agcatacagt atatgggcta accttaattc tttactatta ggatttttct  21600
ccacaatagt atcatagtct ttatttgaat ttttaaaaat tcctgagatc ttggctttag  21660
ctcttagtat atccatctca atatttttgg ggtctctttt cttaatctca ggattacttg  21720
aaaagtcaat tatttcatcc ggagtaatat tcatatgagc caccccctatc tgtttctttt  21780
attcttgttt gtaaatcttc tagcaggttc ttctttactg tcatctgtag aaggtatttc  21840
ttctccagta aaatcctcta gaggttcatc ctcaacaggt tcatctatga caatcacatc  21900
atagttctgc tttaaataat ttactagact atctttaact tcttctacat ggtcttgagt  21960
aattctatga cctttaataa ccagagtttg taatttaccc tttgctaatt tgaccttagc  22020
cataatatct ctcctttcta atgaaaaaga gcccacattt attgtgggcc ttcatgatta  22080
agcttttacc ttgattatct tagcagcagc tttaggatct tcaaacttaa catccatctt  22140
aagagttaaa actacataag tagctctttc tctaggagct ctttctaatt caattctgat  22200
atctcttgag atacctataa ctatattctt agggtgagtt aagattatat cagatacttg  22260
tgtagaagaa tcctcataat cttgtagcat agctataccc ttaacaggta caccataagc  22320
agatttaact gtaccattta taaatgagtc atcaccatta gcagttaatc tctcccctac  22380
taaatctacc caatcagttt ctaaaccatt tgagcagtag aatctccact cacctggatt  22440
tcttaagtac ttagctggaa cagctttctt agcttgtttt aataggtctt tacttaaagc  22500
agctttttga gcatctacta cgtgagctgt taattgtttt ctaaccccat ctaattgttg  22560
taagaaagta tcactaccat gtccagtatc accattaaca attatttctt ccatatcaag  22620
agcaactctc tcagctaata attgcattac agtgtcttct attgattttc cttctatatt  22680
tgtttctata gtatcatcag ttaacttaac cacagctata aattctttag cttgtaaagt  22740
aactgttcca gtagttggag ctgaatattt agactcccct ggatcttttc cttcagctgc  22800
aggatttaat actctttgac caaatcctat tgactcaatc tttttagagt ctcctttcat  22860
tggtacagtt ctagcctctt ttaatattgt tggctcatca attatcattt taataaaagc  22920
gttagcttgt tctgtgttta atttacctcc accatttaat actgtagagt taaatacggc  22980
tttatttact tttgacataa ctttccctcc tagttattat tattcttggt ttccaccaaa  23040
taatccatta aatactgact tttgaacttc ttgtccttct tctccatttt tagcaatttg  23100
tttacttcct acatatggag ccatggcttt agctactgcc tcagctattt tttcttcctc  23160
agtcttttct tcttgtttct ggattaagcc agcctctaac atagcttttt ccacagcctt  23220
agcaactata tcttcagtag tagcttgttg accttcattc ttattaactt caccctcaac  23280
aggcttagtt ccatctaatg ccttttttgat agcttcgtct atcatttttt gtacttgagt  23340
ttcattcatc tcttcttccc cctccactga gtctaataat tcattaatag cactttgtgc  23400
tgtttttaac ttttccacat tttttgaaga tattttctta cctgccttat tgactggtaa  23460
ctcaaaggat ttagctactt cttctggagt tcctaataat attccctcca tagtttcaga  23520
aaattcttga agagcttcct ttatcttatc tacatcactt tcaaaagatc tagtgtaatc  23580
ccaactagaa tatggatata gaatatcttc tagggtacta actgcattcc agaaattatt  23640
tctttttgca gtctctttat atttttcaga gtatgcacct ttctgtatat gctttggagt  23700
taaccccaag gcctttccaa ttttatcaag tatagattga cctatagact tctcaatctc  23760
atcaatatct acatcttgtg tagaatactt accagtacca cccatagacc atccagtaat  23820
```

```
ttcgcctttc tcaatcttgc tccatagatc atcatcgaca atctcagctt tagctaacca  23880
agttccagct ttaactactg taccttctat tgtagtatct tcctcagtta cccatgattt  23940
tacaatcttg acaccctcaa gagtgttctc attgtgttgt aaatcactac caaggccatt  24000
ttcattaaac cactcacaag ctttcttgat ctcttcctca gtcataaagt tatcatggta  24060
gtcagcagtc attggctcat atactacacc aataacaaaa tgattatctc cttcagactc  24120
agactttaag attggcttat catatctaaa tctattagga gctccaagtt ctttagccac  24180
aatccattgc catttattag ctgctttatc aactaatgaa aggtaatcaa ttttagcatc  24240
tgagatctca atagctttct taactgattt tactggcatt tactctccct cctttacaaa  24300
ttatattctg ctatcacttg atctctgata gcttcttttt cttctttaga taatcctagt  24360
atatccttat caattacagg cccatgagta caatgacaat tcacagtctc agaagctggt  24420
aagtttatat ctctaggaaa tctagcttca taaattccta ctgtgaagta ttcaccttta  24480
ttaataacag taccatctag atcgacatgg tgttgccttg ggtgaatacc ccttccccct  24540
gagtgtttcc actgtattcc tgttactgcg gggcattgat taaaagcctc atccttagca  24600
tatgagtggg ctcttaacat ttcagtaata gcagtagctc tagctctagt tctactaaag  24660
ccataagtct cagataattt accaactaca tcttctacag actctccatc ttcaagagcc  24720
ttatccagaa tattctgtag tttttcatgg gaagttaatt tcatcatttc ccccagttta  24780
gaagaccact catctataaa ggtagtagta tatggagaaa agactttggt tagggataag  24840
tccttatcaa taccttgtaa gtaagtatct cctaaatttt ctatagcttc ttgataacaa  24900
ctcttaagag tttctgctaa agaagtatcg atatcatctg tacctatttg agactccaca  24960
tattccataa attcttcaat ggtttcaaag tctccatctt ttataagatg ttttaattct  25020
tctgtaagga gatcagaaat agtgtcttct aattcagaga tcttttctat tgtataatca  25080
atctcctcat agccagcttc tttcaattct ttcttaaggc tatcatcttc attctttaag  25140
atcttatcaa ttttagcgat caactcatca gtacccacta ttacttacct ccttttaatt  25200
gatagtttaa taactgtttc ttagcctctt taagtacagc tatcacctca tcactcccat  25260
tagagttttg agccttctca attatacttg ttaagttatt actcattgaa gaggcaactg  25320
agtaagtagg gatatttgcc cattcttcat caataggagt atagtcctta ttgattgatg  25380
aataatactc ctcattaatc tgattaggag tcatagctct agaggctata gcaaacattc  25440
ctttctgata atcagagttc tcaatattag gactcttaaa ataagcttcc acatatttaa  25500
aaccatagcc agatagaata acattattta gtatccatgt taggttttct ctttcaggaa  25560
caaatacttg ctcttcagtt tttcttgtag cctctctggc tgtagccaca ttgtaatctt  25620
gagagtaccc tacatatatg tctggtagta agaaagaaga ttgtatcttt ttcctagtat  25680
tatccatgta gtcttggaat aactcatcct tctgtaatat ctcagatagg ggcttgacct  25740
caacagtaac tggcttagag tcatcaaggg cagtgtcttt ctctgcagct tcagtttcta  25800
atactaagaa accatgctgg gaattttcac cttttacact attcatgtac tcagttaact  25860
cattccaaga tttatcatta agagtaccac cttgaattag taacattaat ggagtatgtt  25920
taccattagt aaaatatctc cagtttaata attcggcctt tcttgaacct tgagcggcta  25980
acataggacc ttcccatctt ggtgtaccat agacaccata acctgtttta aaatgaagta  26040
tactgttagc tcgatcttta agaggtatct ctcccttttc ataatacttt ccagtattca  26100
tatctagatc tctaggatct ccccattcct taaagaagat tgattgatta tttacagtct  26160
```

```
gcttaaatct tctgaacctt tttcttctag tgtactgttt accatatcta gttacagtgt  26220
actctgtact ctcatcatct agcttaagaa ttttaattgt cttaggatct tcaatttctt  26280
ttatctcttt tacgagagct gagtctttag gatcttctac tatctctaaa aaagaatacc  26340
caagtccttc tctccaatca actatctctt caaagacatt cttggttggt ttatcaaaag  26400
acagggtatc aattaattct tccagctgtt tatattcagc tttcatttct ggagtaggtt  26460
catctacctt ctcaatatac ctaataccta ttccgaatcc agcaatatta tttcggtagg  26520
cctttttgca ttggggtatt attgtagact cccttataat cacttctaat agttgggggt  26580
catactccgg agatatctca tcaacttcaa ttccaagtac actggtttgt tgattggatt  26640
tatccactgg atccaaagac ttttggatag ggtctccaca tatacttctg gcggatatct  26700
ttttcaaagt tactttacct cctttcttac attatatatc aaattataaa atccagatgg  26760
cctcatattt cagggaggat tacatcaact ccacatatag tgtcaaatac ggccattcac  26820
atgatttaaa aataactata atttgatacg tttattataa cataattcac aaaaatttgt  26880
caacgtttta tttttacatt attttccgga agattttccg tatatattcc ccatataaaa  26940
ttatataatt attaatgtat actatattac tatattaatt tatgaaataa attatatagt  27000
atatagtata cttatattac atatatataa aggtggtaac tctgatatgc cttctatatc  27060
acattattac taatatagag cctagtcaat ttcaaaactg atatctcaca tatcagaata  27120
aaaattattg gctttaatgg gcatatcagt tactagattt ttcttaattt agatccaaca  27180
ggaaggcaag ctaagaatag agagtctgct aagtctggag aatgtagtcc ccttttcttc  27240
atttcatcct tactctccag ctttatttga cctttggagt tgaatacttt aaactttctg  27300
gtagtcaatt cccccacaag gtcagtatta ttcggtagcc ttaactcatc atcctccagt  27360
aattccttaa ctacagaggc tatatatgtg gttgtatcat aataaaaggc ataagcctgg  27420
gacccccctct ttaatggcat accaaactta catggtacta ccttcaacca gtccagtttt  27480
tcttcaagtt ttatctcttt taatctatca gttactcccc cacctacacc agtgtcgtct  27540
atttttacaa ctacagctag tttagggaac tcaccatgca gggatttagc ctttcttagc  27600
acttccccta ctgttttcat ggtgtcctta ccttgatagt agataggttc ttccacatat  27660
ccatcaattt tggtcatgat tgaggtctta tctgaaccaa atctagctac gtctacaccc  27720
atatctatag taactggttc tgtaggtctg gttatttcac tgttgatacc tctatatact  27780
gtggataatt gtataaatat gtcatcttct tctagtggaa agtccccttt taccagacat  27840
ctgtagacat tggactcttc cccatacttt ttccttaaca ttttatggtt ttctttatca  27900
gttctatcaa cttttgtagc gtcaatatga atacatttaa aattttcctt aagactgtgg  27960
tgagaatcaa agaagatacc tgtattttta acagggttac caatcaaaat tatcttattt  28020
tcctcatctg atatagtacc aagtaatgct tctagtatct catcatctat tccaggagcc  28080
tcatcacata taattagcat gaactcacta tgaagaccaa gcatattctc ttttctatta  28140
ctagttttac acatagcaaa ccaagtcata ggactacaat tcctagtcat agtggttttg  28200
tttactgtaa agtaatcttc cacaatggtt ccttgtagcc attttgatat ttcaggccat  28260
aatacagatg ttaactgtga aaatgtagga gctgtggcaa ttaccttaca ttcaggccta  28320
aaggtcatat accaaattat aaggcaagca caggccatag tcttacctac cccctgtcct  28380
gaccttacag aggttctctt attgtctctt acacttatta aaatatcctt ttgatgtgga  28440
tctaagtgta ctcctagtat atcttctgag aatccacaag gatcgtcata atatagatct  28500
actaattctt caaaggatat ttcttccagg gcttccttgt taatgtggaa cttatcaact  28560
```

```
aaagcatcta gctctaattt ctcaatcatt ctatctaaat caaacaatta tatacacctc  28620
cttagtaaag tgctttattt agtcctgtaa taccttttta cttagtagta ttagattttc  28680
ctttacctgc attctttttc tttctatcag ccattttagc tctaagaacc tcaagatctt  28740
ttcctttgcc agcattattc tgattttcct gtatttgtaa aagtaattta accttttcaa  28800
gttcaacttt catcacatca gtacttaagc cgaagtatac ctcaagtctt tttagtgcct  28860
gaagtctatc ttccatctta actgataccc catctttact ttgtttaatc tcattgatta  28920
aagtaccatc tacagcctta ctagacctta atagtactag atcatccttg aattggcaca  28980
catcagttat atctgcaaag gctatcttca tgtactgcct tattacatcc ataccatcgc  29040
atagtaattc ttcatctcta tcggctctga tagcctttag agcttcctgt attttcttct  29100
tctttaatag tttagatcca tgtgcatgag aattattcac aggatagcct gctctagcag  29160
ctgctgtagt tgcattaaag cacttcatgt aatgaaatac aaacaactct tctttctcat  29220
caagatcata cttctcagcc agggtcttaa tagtcttttt tgttttgcta ctcaatgcca  29280
caatatcacc ttcttcttct aaaaatgtta tgccctgttc tttaaactct cttagacact  29340
gcctaacaaa ggtctgtgat accttagcaa ggttccttaa ttgtttagga tgtgtaaagg  29400
gatcagcctt cagggcatta tatatcaatt ttttggcttt cctcaaatgt tcaggagtac  29460
agtactctgg ttcagtgtat gacttatagc tcataataca atatcacccc cttaaaatcc  29520
agattttact acgtgaaaaa tggttggcac actaacatta atgctagtaa taccaaccaa  29580
atggcaaaat taactatgga tttataccac tattatacca catctggatt aattatgtca  29640
acgttttata attttacttc acctgtcaat atttttttcat acatatccac atctattctt  29700
ccttcctgta gcaggttatc agctgcaatt tgtatttctt ctggggaata tactggatta  29760
cctttagtat caagttccgt accagtatat gagtctacct tgcccctgtt cataccatat  29820
ccaactgatt tatgaacttc tagtttttca ttatggtctt cttgccaatg ttttaattct  29880
tcctgatatt ccttattctc ttctttagtt tgtttacatt caataggtct attatctttc  29940
atcttttgct ttagggctgc tgtattaggt ttacagttct tagatcctcc acctgaacct  30000
ctattcttat cttcctcata agctttatta atctcaaccc caattattag atccatcttc  30060
tctatcaagt aaagacattc ttttactatt ggattgttag gttgattttt agaaatgatg  30120
tcttgacact ctttctttaa ttgatgtgga ttattacatt ggctagggca tttttctcct  30180
ggtccatagg gaattgtata tgctaagcag ttacctgctg gatcccttct ataacatctt  30240
ctcttacata ttattttact cattgttgtt atcctcctta aatgtaataa atattgctct  30300
tgatactctg gaaatgttac atccttgaaa tgcttctctt actttatcat gtactagatc  30360
tacccctact aaaggttcta tcacaactat attattagtt cctagtacag gaaatacttc  30420
acattcagta tctagtccat ctataaattc tttaacttct tccaatcctt taactggaac  30480
tggcttaatc cttgggcttt cttcccacaa taatttttct ctgatatatt tttcttctga  30540
taatctatca aactcatcaa tgttacttc ataaggattt ttaatttctt caatacctgc  30600
agaggccata gatcttatgg cctttaattg actatcacta aagaattttc ctttactcat  30660
attgttctac ctccacatca ttacaaatta atttagctat tcctccactt aatctgtatt  30720
tctcaagata taccactttc ttaattcctg cattgattat taagttagca cagctctcac  30780
atggagataa ggttacatac atagtagttc cttcagttga gatcccatgt ttagcacagt  30840
aacttattaa gccagcttct gcatggatca caatatcaca tccaggacct aaacaagttt  30900
```

```
tacaatgttc tactcctgaa ggtactccat tatatgaagt agcaactatc ctgttatctc  30960
taactaatac acaaccaact gcttttctta ggcaagtaga tcttcctgtc ataagtttag  31020
caacttccat gtaaagtgtt tctctgctta ttctgttgtt attattttcc atagtttatc  31080
acctcaattt tattatatac tattccctat catatgtcaa gagaaacttt agaaaggtat  31140
atcaccataa tccagatcaa tacattgggc tggctttagt tttacttttt taggctctgg  31200
agttttcttg actttatgat actttggagc tctggctaaa tccttttttta actttctgac  31260
tctcttcata tcccactcat gtatttcatt gtctctaaaa tattcattca atactcttac  31320
tgcggatctc tttgaaggtg tctttataga gcagttatta ggagcaagac agcatcctgt  31380
ctctttatct gatatagtat aacatactgt attataaggg gctcctacgg gcctatgaat  31440
gaataaggtc ctgcccatat aatcaaactc acataatact tccacatatc ttttatactg  31500
ttgtccttgg tcattcttac atagtatata agtatattct ttcatgttaa ttctcctttc  31560
tatgttaaaa gggagatcat ctctcccctt aatacctttt tattcttctg ttgttctcat  31620
caacctcaat tacttcatac cttctaacct tatcagatat accttcttcc tgtaatactt  31680
taggaatata tcctatggcc tgtcttttgt tatccacttc aaaatatctg gtcaagatcc  31740
tttttgatgt tacaatcact aatcttactt tcatatcatc tacctccatg tggcctgaac  31800
tacagctcca ggtctatgct tagcttcaat cttagcttct tcctcagtat caaaatagat  31860
tatatcttcc ttgtgttcat ccttaacaga tacccagtgt actcctaaat atttgttatg  31920
tgctaataca ctaacatcag ggttccaatc cacatcaact gttacttgta aaacgatata  31980
tcttcttttc atatcagttc tccttcttgt atttatttgt tgattttatt ataagagagc  32040
ctcggaagtt tgtcaaagat tttctcgaag aaattcgtat aatatcttcc gagctgagca  32100
taatatagac tataaaaaca aaatcaagga gttgtaataa atgaaagata ataacttaat  32160
accattaaga gatattgcca aagaggttgg aataaatgaa aggaaagcca gaaagctatt  32220
aagatcacat gagaataaag caaatcacaa ttattattgg atgtttacac caagagagaa  32280
aagacatatt gtatcagttc taaagagact gcaataggtt ttctaaaaat aagggaggga  32340
ttaaccctcc tttttataat tttttgagtt ctggaaaaat ccttaattag ttcaagtttc  32400
gtaaagttct cttgatcttt tccattctct tcttaacttg gatagcttct tcttcgcaag  32460
gagcatggcc atctaggaat tggtgccatc ttccttcaag ttctctgtat tcagattgaa  32520
gttctataat ctcaagtgaa tgattgtcca tactatcacc tcctcaacac tattataagt  32580
gatactgtca tattctgtca aataaaaaag agagaatgtt attctcccca tcttaatatc  32640
tttatggttg ctccatcaac tcccttgcca tccacatcat ggacatactt atcaagtctc  32700
attgttgagt cctgtataat tcttttgtct tctctgtcaa aaaccttaat gacatcaggg  32760
ttacccctgt caatgatgta agcaatctct tgagttccat ctgcatatgt tacttgaagt  32820
aatgaatgta gaggaataaa gtctggagct gcccagtcac caatcttaag atctcctcct  32880
atactattct tggtctcata tcctgccaca tctgtaggct catctgatga gtaataagta  32940
acttcaactt tgaactccat tcctttaaat gagtttatca tctcaattag attttgttta  33000
tcagttctca gtttatcatt ctgatatttt aatccttcta cattgtccat cagtatctca  33060
gtctgctcag ttaattgttt attcgactca atatattctt ggacagcatt tccccaatga  33120
ttgtttaggc tctgtatggt taacagtagc cctcctatca caattattgt tagtaatgac  33180
ataactcttt taatcattct cttttaactc ctttattttt aatttgaatt tctcaattcc  33240
agatttatat ttacccacag tatcaaaggt atcggttagt attgcatagg tttcctcatc  33300
```

```
agaattaaat ctgaagcttc ctctcttgat gtctcctagc ttattaaagg tcttaccctc  33360
cttgtccaga tatcctttat agtccatata gcacagacaa gcagtaacaa actcttgctt  33420
attcctgaaa ttatgcttga tacccatacc atctacccat ttacttaata caaataggct  33480
ttcattggtc ttttttactt tattattctg gattagatcc ttccacacat aatcattagc  33540
ctctttaaat gacttaaatc tcttgccttt tagtatctta ctactctgga tcttggcttt  33600
ataatcctca aatatacttg gccagaagtc ttttagatat aaatacaagg aaatatcatc  33660
taatttagca ttcggatcgt taatctggat tacaggatga ccatccattg ctctgatgtt  33720
attccttaat tgggtattct ctctttttat tttagatact tcaatatata atttaacgaa  33780
tgcgtcagac aattcatgat tggttaattc cctttttagg ggcttaccat ctttactttc  33840
tttagtagtt acaatattaa agtagtcttg taacctatcc cagttattct tcattagatc  33900
cacctcctat gcttacatta tacatatatt gtactgatat gtcaaagtcc aggcattaac  33960
tgatatctga tatgcctata tttttacccc atatcagtct gatatcccac atatcagttg  34020
aaactacaaa atcacaaaag cattggtatc actggcgtag agggatatca gttatgcccc  34080
ctttatatat acatagtatt atatatacta tataataata tattattata tatagtatat  34140
atatattaca tgtggtgata caagggcagg ctattgcctt gcctccatta tcattacggc  34200
aggcatatcc atgcttccga gcttttgccc tatatagaaa aacccagacg gtcagcgatc  34260
gagctcttga ttttagttgg aaagagttct agttggaaga agagtaaaga gagagttctt  34320
ctccagttgg aaagagagta gagttctccc gaacgttgac agtagtaatc acttctctta  34380
taataacagt aaaggaggga taaccatgat gaaagttata ttatctaatg aaaaagagat  34440
tatcattgaa aacaaggact tcttcataat aatggaagag gacagattta ttctatctag  34500
agcaatagat aagaatagcg gagaactagt atctcaagta cctaagtact gccttcttat  34560
atatgaggat aaatctatac caagatactt atataaggat aatactcact tatatgaggt  34620
tattggtaat agagctatca taagatacag tatataagag cccacaatca attttaaagg  34680
cctcttaaaa taagataatg tattttaatg ttctatacca ttagaattga ttacaggagc  34740
tgctagaggc ctttaaagga tatataggag gtactactaa tatgtataaa ttatacctat  34800
gttacaatac taatgaacaa aaacattatt gtggtattac taagaataat attgtggatc  34860
gcaagatatc aaaaaagctt gattgtaact tcacactaat aatattaaaa agtgataata  34920
ttaaatatct ggaaagtata cgagataggt taaaggggga ctataattat cgaaagaaaa  34980
gggtatacag aaaaagcact gaacagtatt ataatactaa acaagaagcg gctagagata  35040
atggcttaac tatgttacaa cttaaaaatt tattgaagga gggagttgag tacacttgga  35100
aataaataca atgtatttat gtaatggtaa aatagtcaag aataaaaatg acttaaaaga  35160
taagtttggt ggtaaatcag tagtattcat cgatggggat gtagccacag taatggactt  35220
tagtgacgga aagccaaaga taacaaaata tcttattagg gaggtatcac atgataaaca  35280
catcattatt gaagagactg gaagggatag aggaaaagca taagcaaaat actgatgaga  35340
taagaaagaa cctaaactat gccagatatt tgattgagaa acagtattgt catttaacaa  35400
aagaacagaa gataagattg ggacagttct taggattgac tgagaagaag ttaaaagaaa  35460
tacaagagat aaataatcag ttaataaatt tgagagtggg gctaagttat gaagtcgtat  35520
gtaataacca aaaaaaatag tggggtatct ttagcagata cagacatggg acaagtatta  35580
gctaagatac tatgtaagca tgggggaaca cttaccattg aggaaattga accagaacat  35640
```

```
attggtcaaa ctttttctat tgtagaaggt aaaagaatat ggtataatag aaaaggaggt  35700
gataatattg ggagaagaa gtgctatgtt aattctcaag tatgactgcg aagaaactcc  35760
agaaagaatt gaattacgaa agaagtggtt acagatttgt cttcattcaa taatatatta  35820
tagatatgac aacaatatct ggacagacca acaatgggat gagactgcca gagaggtagt  35880
taaacttaag aatgagaatc caggtttagt aaacagtatg ccatttagga atgaccttaa  35940
agtctttgat ggatccactg gctttaatct ttcatgtatg caagatatta agatgctaag  36000
gtgggctcaa aacttacttg actttcatgt taaacgagga cttgatggaa agagtaagaa  36060
aaagaagaaa aggaggagaa agaaatgaac ctacttgagc attatataaa aaaggtacac  36120
agtgtaagag agtaccatga atttgataat gaaccttggg ctaaaggtaa acaatatgta  36180
gaagtagaca tggactatat ttgttattct aatacaccac aaagagtgaa gatggtattt  36240
actgttgatg agtgggagaa aataaaatat caaggctact acatgggata ggaggaatag  36300
ttatgataag agaaatgggc atgagaatgc taataccaga aatacatgat ataaaagata  36360
gagatataca aaattttgta agaaaggccc taaatgagct agttgatgaa aagttcttta  36420
taatacctgc aagtagtact ggaaaatatc atccaactta tagtgcaggg gtaggaggtt  36480
tgttaagaca tactaaagct gcttgttata taggtaaagc attatgcgaa gctgagatga  36540
tatgtcagga agataaggat ctgatacagg ctgctctgat attacatgat attaataaac  36600
ctgctaagga gcatccatac ctagttagag agacactatt accactaaag gaagagtttc  36660
catcaaccta tgaaaaggta atagaactaa ttgagtctca tcatggtcaa tggggagagt  36720
acccaatcaa tacttatcaa aagagaatag tacacttggc tgattatatc agttcacaga  36780
aaggattaat attctcatat gaccaaggaa ctgattattc tgacctgtta tgggaggaga  36840
agtaaatggt gctaggggta ataaccctag tatcaatatt tttactagga gtgtttatag  36900
gttttgaggt gaagaaatgg aactaggatt tgcaatatta gctatagtag tatcaatatt  36960
tttagaaact aaatatataa aggagtagat tattatgtca agagcaagag ctgcaagaag  37020
aagagctgaa agagagaaca aaaatcttaa tgttcttaaa gctgtggaca tcatgttagc  37080
cttatcatgc tatacactaa agaaggaagg ttatggtaag actagaatga ctaggtttgt  37140
ggaagggatg agtaaacaca cagaggagat tgagaaggga acacttaact atgaaaccat  37200
aatgggagag attaaggatt tagtaccacc aggtatattt gatttagagg aggagtcaaa  37260
ggagtgatag tattgggata tttattatgg gcatttagaa tattaggcat acttgtaata  37320
gtatggtgta taatggaggc gatcagttgt gagcaataag ttatatttta gatatagtgc  37380
tatgaactct ggaaagacta ctcagttaat ccaggtagca cataactatg aagaaagagg  37440
aatgaagcca ttagtagtta agcccggaat tgatactaaa ggtggaccat gtataatcag  37500
tagaataggg gtagcaagaa aggtggatgt tcttctacct cctagagtta aattatcaaa  37560
aatactttct gactttgagt ctaattattg ggcagtagat gttatattaa ttgatgaggt  37620
acaattctta tccagagaac aggttgatga tctgttaaat ttatcattac attatcctat  37680
tatatgttat ggattgagaa ctgactttaa aagggaagga tttgaaggaa gtaccaggtt  37740
attacaagtg gcccataata ttgaagaatt aaagaacatt tgtcaatgtg gtaaaaaagc  37800
cacattctca atattaaaat accagggtaa atatactgac caaggtaacc agatacaaat  37860
tgataaccag cccgaaagtg ttgaatatga agccgtttgt aatgaatgtt ataataaatt  37920
aatttttct aaataactcg ttgacaggct atatgggata tgatattata gtattgtaat  37980
caaattacaa acaccaacca aaactttata attagttaat ttcaaactat actaaatttg  38040
```

```
ttatttaaaa attaaaaata tggaggaatg attattatgg caaaaggaaa agcaaaatgg  38100
ttagaggaag caaacaataa ggagctaatt gtaatcgtac aatctgcttt aaattctgga  38160
gatgagaaag aagttaaaaa ggctttaaaa gctattgtgg aattagatga aagaactcct  38220
gacacagatg gacaaataac tgtagaggaa gcattagaat cattagaaat ggctgtagga  38280
actgtaaagg ctgcatacca agcagaaata gatgctgtgg aagatgaaga tgtagtagat  38340
gctgacttcg aagaagttga tgaggacgaa gcagaagaag acgaaaatga tttagaatca  38400
ttatctaaaa aggaattagc tgctatggct aaagacttag gtatcaaagg agctaagaaa  38460
aaagataaag atgagttaat cgctttaatc aaagaagctc aaggtgaaga agaagacgaa  38520
gaggaagaag aagaggatga aactcctgac tactctgaaa tgactaagaa agacttaatt  38580
gctcttgcta aagaaagagg aataaaagtt aataagaaaa tgaaaccagc tgagataatt  38640
gaattattag aagctgatga tgaagaataa ttctcatcaa ataataaggg gagcaaactt  38700
gctcctcaaa ttttttactt attttagaaa cagatgttag agggggatgt ataaatggca  38760
agaggtggaa attcaactta tactaaagca gtatattgtt acaacaataa tagggagtat  38820
agatccttca gatatgcagc taaacagtta ggagtatcgg ctgttagtat aatgagagta  38880
gttaacggga ctaaaccaca tatagggga ttagtattcg ctgagataga ggaaggcact  38940
agaaaattaa agccaagagg agaagtagtt ccatacttga aagaattagg ttgggataat  39000
atagacttat aatagggggt ataatatatg gacataaagt tcttgaagga tatattctct  39060
aaacaatgtg aaaatggaga ttacattatc ctagcagcta gaaaaggtaa agaatggaaa  39120
gatgtaccaa tcaaatataa taagaataac attgacaaaa aactaaagga ctttgaacaa  39180
cagtataagg gttatgattt atattggagc ccaatgccct atagtaatcc tcaaagaagg  39240
atagttaact tcatagagac taaatactta atacaggata tagatgagca tactgaccca  39300
ttagggatta aacctaaacc aagttatctg tgggaaagtt ctcctggaaa atatcagggg  39360
ctatgggaaa tggataggta tatagaggct aatcaatatg acgaaataaa tccagcctta  39420
gctaaacata taggctgtga ctcctgcttt gatgttactc atgtatatag aataccagga  39480
actattaact ataaatacaa gaataaacca aaagtaaaaa gacctataca cactaaggag  39540
atatataagc ctaaggtgat cgctaaggct gttaaggctg taagtaaatc taatgatagt  39600
gttaaggtca atataggagg atctgaggcc tcacaatctg aaagaaagat atatgctaaa  39660
tataatatac ccaagaaggt tagagactta ctggctttag atgatattac ttctttagat  39720
agaagttcta ctatatggta tattgagaat aaattacatg aaataggact agagcctaat  39780
gagattatat tattagttaa gggctcagct tttaataaat ataagggaag aaaagatgaa  39840
gaaacaagat taagaaaaga attggataaa atcataggag gagaaataga ggctgatatt  39900
gaaaaggctg aaagtactaa actgagaata gatagttatc aggatgttat gggtaataat  39960
ggagccttcc ctggttggtt agtacaaggt ttctggggta gaagatctca tggaattgtg  40020
gctggacaac caaaggtatt taaatccaca tttacacagg acttagctat atcagttgct  40080
agtggaagac cattccttgg tcaatatcct gttctagaac ctggcccagt aattgtagtt  40140
caaaatgaga atgctgactg gattatgaga gatagaactg aaaagataat tagccacaga  40200
ggggtagttg gtaatgtgga tataaaaggt aagagaagac ttaaagttag gtttgctcca  40260
gatcttccta tcacttttat taatcaacag ggatttatgt tagatgaaga atcccataga  40320
aaacagatag aagaattaat tgatgagata aaacctgtac tagtaatatt cgacccatta  40380
```

```
tatcttatgt ttagtggaga tcttaataat gcagctgatc ttaatcctgt actacaatgg  40440
tgtcttaaac ttaagaatga gaagcataca ggagttatgc taatacacca ctataataaa  40500
ggtggaaatg ctactcaaac taggggtggt caaaagatgg ctggttcatt catattacat  40560
ggttgggtag aatcagcact atatttaaag agacctgatg acttagaagg tgatgatgag  40620
gaaatcgagg tagatataga taaccttgat aaacaaagcc atttaccaag taaaatcatt  40680
atggatagag agttccgtct tgcaggacaa ttccctcaaa ttgaattgaa cttatcaatg  40740
ggagaatttg gagatccata ttatcatgta gaagtagcaa tacctggaaa agaagtaatt  40800
gtgaaacctg aggacaaagc caaagttata gaggctgtaa aatcaggagc tcataccaag  40860
gaggagatag tgtcaatatc aggattaaat tcacagaagg ttaatctagt tctagatact  40920
ttaaaagata ctattgtata ttctcctgat aaaggttata atataagtaa gaaactaaat  40980
attgggagga aaaaggcatg ataataaagt gtaagaggcc agcaggtcat aatcatataa  41040
aggcctttgt agtagtaatt attgctagag gtaagaagaa taaaatcact tatcattcag  41100
gattgaaata tttctatacc tataaatcag ctaaattatt tatagacaaa gttatggaag  41160
aatgtccctg ggctgaattt tattgggtgg atgtccatga agctcataag atccctgaag  41220
gcgaagagat acctaagaag aagatgtggt gtccgtattg tcaaactatt caagaattta  41280
agagaagcca aggaggttac aagaattgcc ctatctgtgg cataagtgac caagactttt  41340
atgtaaaatg tatgaatata aagtataggg aggctaaggc taatgcgaag aagaaacttg  41400
aaggaagtaa tactaattct agggatatca ttgtcaatgg agataatgct aactcagggg  41460
gcaaaactaa tagaaagtca tcaccaaaga aaaagtcaag aaaagttagt agaaaagctt  41520
cataatgctt tagactataa tgttattgag acttctccat ctggactaga tggggaggat  41580
cttatcatca aactaaacct taatagtcct aaagacctta cccctaacaa tttatctaag  41640
ttagctaatg aggttatggt caataactta ggagctcaga attatactat acttgtttat  41700
gatagtaata gaccagaaaa tcttctggct gttatagata tacctaaaaa ttctaaaata  41760
acctttgaca taataaatta attatggtaa tataaaaatg tagaaggagg agaatttaat  41820
ggtcaataaa aagtattaca tcttgaaaga ccttaatgat gacaaacccc aactatggaa  41880
gggaagttta accactgcta ctaagatagc aggagcatta ggagttagtg tgataaaact  41940
aaataggtat ttagtaagaa agggatttgc cagaaggtac aatgaacata cactcgaaat  42000
agtagaccca atccttgcta aagaacttgg ttattatgta actccaagta agtcccttat  42060
aaatccttta tttgaatata atgataaagg agtacaatat atactaaact taatagtaga  42120
agatctaaag aatggaggag agctttaatg attatcattt taggaatgga taactcaggt  42180
aagaccacaa cagctaagaa cctaactaaa cacagaggag gagaatatat ccaatcaatg  42240
ggacctggtt cttatgaaga acaaagagaa tgggtattaa ctcaaattgt gagaaaaagt  42300
gaaagggaag ctatacatga tagatttact tgctttgaag aaatggtgta tggacctatc  42360
atcagagata gtagtaattt caaccttgac agtaaggagc taaagatctt aaaacattta  42420
tgtaagccaa ctattgtata tgctagacca cctagagaag tgatcttcaa ttttggtgat  42480
agagaacaga tgccaggagt aattgaaaga gctgaacatc tactggctag atatgatgaa  42540
ctgatatgga agttattctg tgatggatgg aatgtactgg tatatgatta tactacttcc  42600
aatgtggaga agttatccca attaatagat gactcaagtg ctaaagaagc tataaaccaa  42660
tttataaata tatcaagata agaggagaga ttgttatgaa tataaaccat gcagtagaag  42720
aaaaagtaga aggagataga ttacaagcta tctttaatag acaaaaggaa ttgatggaga  42780
```

aatatcatca tatagaagct aggtcaggat tatgccaaac tgaagactgt ccagttaact 42840
taaatgataa aagaggtcaa gctagactta aagattttgc ttggagaatg actgaagaag 42900
taggagaagc attagatgct tataatcatg aagaccatta ccaagaagaa ttgattgatg 42960
gattacactt cttaactgaa tttacaatcc tagctggtaa ggattataat actatagatg 43020
ataatgctat attagttgat agcctagaga acttatatca taaggctact acatcaccag 43080
aatttcctga aatgttagta gaagaagctg taactgacct ggtaagagaa atgggtatgt 43140
gctgtaattg ccttaagaat aaaccttgga aacaaacttc aatgctaaca gatgtaaatg 43200
cttttaacca aagactattt aatgtatggg tatgttatat taaattatta gctgtatctg 43260
gcttagaggt agatgacata gtaaatatat accttaagaa atcacaggta aataaattcc 43320
gccaaagatc taattactaa aataaatact taggagaagg taatatgcta ataagagact 43380
ataatgattt tgatgactta ttcttaaatc ttaataggga aatgattacc aatccagaag 43440
aaactatgat gtatactcag aatatacagg gctttcagga ggacttagtt ctctcctgta 43500
agtcccataa atgtacttta aatctagggg actttggata taaagaaggt aagtggggac 43560
acctattaag atcatacatt gattatccac aattaattga atttagagaa aagcttacca 43620
agataagtgg tatgagctat acctattatt tcaacaggaa aaaagctact aatggttctt 43680
gcttgatagc tgcagtagta actagaccaa aaagaaaagg accttggaaa cacttaaaaa 43740
ttatgtatag agtatgtgaa ttacaaaaga aattcgcagc tgatctggta ttaataaaca 43800
ggttcattga agaactacct caagaagtat gtgagataga taatattact tttcatatgt 43860
ctcaagctta tttgtcagga atgtttataa atggatactt caattatttt aaggtaccaa 43920
gaaagagtat tgctaatagc aaacatcctt ggcataaatc cttgaatagt aactataaca 43980
ggttctttaa atcagaggac cagatacact cttacaaagc tctccagaag atgcagttat 44040
tacattttgg tctggagaaa tttccaaaga tagatatcaa taaattatct attgacaagt 44100
actttaataa gtagtataat taacttaaca aaattaaata aatggaggaa ttaaactatg 44160
agaatttata ttaatgctca agaagcattt gaagaagtaa aaagagattt atgtgaaatg 44220
gggattgagg taagacccaa aactatgcaa gataaagtta tagaaggtaa tccagattat 44280
ttcacaaagg agttacaaaa ctatagttac acaattctag aaagtaaacc tgaagaagtt 44340
ccaggtgtat ctcaaccttg ggcagatgct gaatttagag aaaggatcta cgatccacaa 44400
ggtgtcatca atcaatactc tcttgaagaa agagaagaat tatttggtat acatccacat 44460
catactaggg gggctttcat aaatcctggt aaagcttatc aattaagacc tgaggtatgg 44520
aatgaatatc taagagatgg aaaatttggg tattcttaca atgaaagaat ttggcaatac 44580
agacaaattg aggatatcat caatagaatt aaagaagatc caggctcaag acaattatgg 44640
ttatctctgt ggaatccagc tattgatcca ttcaatatag gaggagtaac tagagtacca 44700
tgttcattgg gatataactt ccaagtaaga gaaggtaagc taaatatcca ttatgttatg 44760
agaagttctg attttgctac tcactttgct aatgatgttt atcttgctat gaaactatta 44820
cattgggtag ctgaacaaac tggctatgaa ccaggaagtt tctctcatac aattttctct 44880
cttcatgttt acaacaaaga tattaagggg gtattctaat aaatgagtta catgagaaaa 44940
gaaagatata aacattctga tcttaataat aaggttaaca agaaggaaac cctaaagcaa 45000
tttattagga atactgaaaa ggaatttgat ttagaaccag ctaaccttgg ggacatgact 45060
aggaatgaac ttaataacta tataaattat atggatgaac tgtggagtaa gtaatatgta 45120
taattatagt gatgataaca gacctaagaa caataacaat ggctgtcttg gttgtttaat 45180
tataatctta gcagctatag gattatgggt aataattttt gatattgcca atataatata 45240
tcatatgata ttctaaattt aaagggggct atcctaatga aaaatataat ttgtcctatg 45300
tgtaaaaact cagtaacatt aaaaagaaaa tatggagcta tgttttggat catgattttc 45360
ttaactggag gcctatgggt agtaaccata cccttcaaaa aacataaggt ctgtccagta 45420
tgtaactcaa tcataaaata aagataaggg cctttagggg tcctttctat ttaggaggta 45480
atattttaaa tgagatgtaa caactgtaac ctatatactc actcagctcc ctcatgtata 45540
gaaggaactt gtgtaggaaa gaaaaagaag ccaagaataa tggtcataaa tagtttagct 45600
aatgataggg atgaggccaa tagaatagct actcctgata aatcattact tgataaaatg 45660
gaaggtctag acttttatta taccaatgct attaagtgta gaactcctaa gggtactaaa 45720
atcaaagtat cagagattaa gaaatgccaa gaacatttac ttaaggaaat tgaaaaatat 45780
aaacccgaat atgttatgat cttaggatct caagcattaa agatgctaag taatgaaggt 45840
ataacttcaa tatgtggagt acctaagaag catgagaaat atggctttaa atttattgcc 45900
agctattcac caggtgtagt tgcatatgac ccaactaaag cacaatttgt agatcaggcc 45960
tttaataact ttaaagccat ggtaaaaggt aaagagcatg aattaccaga gcttaatata 46020
aaacttatta ctagtatgaa agagctaaac caggctttca aatatttaag ggatgaaggt 46080
tataatagag tatcatatga tatagaaact agaggcttag ataggtttaa taatgacatt 46140
acactatttg gttttggtaa tactcaagta cagtatatac tgcctttaga agtcaaatat 46200
agcccactaa ggggtaagcc catagcacaa agaagattag ctaaatcctt aattaaaaga 46260
cttaattctg agatgaagga aagaatagcc cagaatggta agtttgatga taatttctta 46320
aaggagaaat atggtattaa gccaatcata acctttgata ctttactagc ctcacattgt 46380
ttagatgaga atactcctaa tggtcttaag gagaatgctc tattacattg taatgctaaa 46440
gactgggata taaataagaa attaaagact ggaaatgtgg agactaaatc agactttgag 46500
gattatgtta gatatctggg atatgatata tactatacat ttgctctata taaaatattt 46560
aataagagac ttaaaaggga tgagagctta tataaattat tccaccactt atatatcccc 46620
gctagtaaag cttatgagga tgttcagttc aagggtatat atgtaaatca ggagaaattc 46680
aaagaggttg aaaaatactt aagatctgaa ctagataaga ttgagactgg acttaagaag 46740
tatactaatg gccaggatat taactggagc tcacctaaac aggttggaga atttttatat 46800
gatacacttg gtcttcctgt gattgaggtt actgactctg gagcaccagc tactggagaa 46860
agtgtattat taagactaag agataaacat ccagcagtag aactactatt acagcatagg 46920
ggagttcata tacaaatttc tcactttata gatggttggc taaataggat gcacaatcat 46980
agattatatc caaactttaa acttcatgga actgtaacag gaagaacctc aagtaataat 47040
cctaatctac agcaagttcc tagagataag aaaatcagga gtttattagg accatctcct 47100
ggaagagtat tcattgaagc cgatctatcc caggccgaac ttagaatagc tgctatgatg 47160
gccgatgagg ataatatgaa atttatttac cagactggtg gagatataca tgactccaca 47220
tataatatta tatctgggga agatatcaat gatgagaaag atccagcagt taagaaggag 47280
aaaaggaaaa aggctaaggc tgtaaacttt ggtttcctat atggtatgca atggaaaaag 47340
ttcaaggatt atggaagaga caactatggc cttaaattaa cagatgagga agccaaaaca 47400
tatagaagga acttctttaa taaatatcct aaactattaa catggcatga taaacaaaga 47460
aagattgtta aagccaatgg tgaagtaaga tctccaatag gaagaattag aagattacca 47520

```
gatatatatt catctgatag atctaaagct gctgaagccg aaagacaatg tattaactca  47580
cctgttcaag gttttggttc agatatcact ttattaggcc tatgtgagat cacaggctat  47640
gctaaatatg ttaatcctga atatgtatta gataagtcta agtttgatgt attaggctca  47700
gtacatgact caattttatt tgaagtagat aaagattatg tggaagaatt agcttggaaa  47760
gtaaaatcaa tagttgaaaa taataaagta ttaaagaaag tatttaagtt taccccaaca  47820
gtcccaataa tcatggatat atcagttggt tattcttggg gaggatgtgt tgaactggat  47880
tttaaaggtg attggaaaag ccagataaga aaagtgttga cagatgaata attatctgat  47940
aatataaata ttgtaatgaa aaggaggtat aaggatgtta aaaataagta attccagaat  48000
taacaaattc ttgtcttgtc cttatgccca ttatgttaaa tactatgaag gtctggtacc  48060
taaaagaagt ggagctgcct tacaaagggg ctctgctatc caccaggcta tagaagacta  48120
ccataatggg aagagttgga aaaaatctgt tgataaattt tccaaagagt tttacaaaaa  48180
tacatttaaa gaagagatcc ttgaatttgg agatattcca aaaatggttt attctttatg  48240
tgataactat ttccactatt atgatgaaaa agaagataat gtaacctatg tggaaaatga  48300
acatcacttc gaattaaaac tatgtaaggg tgtaactcta gaaggctata ttgatagtgt  48360
cttagatgtg gatggaaaga tatgggctaa ggaaactaaa acctacaaaa agatgcctga  48420
tagaaatttc ctgatcttca atagacaatc tgctatatat acctgggctc ttctacatga  48480
atacccaaaa gtaagtggta ctatatggga tataatatta gctcagcaac caggtagacc  48540
agaattaact caaaaagggg tattatctca aaagaggatt aaatccacac ctttagagtt  48600
agaaagagga ataagagaat taggattaga tcctaaagat tatgagtctt atattaattc  48660
tgctagatgg gaagacttct ttgtaagaca cccaataata ttatcaaaga atatacttaa  48720
cagtgtaatg gatgatacta ttgagatagc taaacttatt agaggtgagg gccacaaaag  48780
aaaggaaaag aaccttggaa aaggttgctc tttctgtgaa tataagtctt tatgtcaagc  48840
tgaactttta aatcttgata aagaatttat tattaaggct gactacaaac aaagggagga  48900
aagtgacaat ggcaaaaaag caaaaatcaa aatcaaatag ttttgaggac agattagtgg  48960
atctatatga tatagatgag cccacaatac taacacttta tggaagatct ggttcaggta  49020
aaactactat ctcaggaaca ctacccaaac caatattctt tattgatgta aaggacaaag  49080
gtactctatc agctagaaac aagcttagag ttaaaagagg agatatacaa gtatttagtc  49140
taaagagttt tgatgacata tacgaggctt atgattacct atcagaaaac actgataaat  49200
ttaaaacagt agttatagac catttaactg ctttacaaga attaggtaat gaaaaggtca  49260
aagctgaaga aggtaaggac cagatgagcc aaagaatgtt tggaaatgtg gctaattata  49320
tgaaagaggt tataaacctt tataaagaat taaatgagga aggtatacta ccatgcttta  49380
tagtacaaga taggttagaa tctggtgatg gtgaaggaga agaccaatta atgcctgagg  49440
taggaccagg attaatgcca tctgtatcta aatatttatg tgctgtatca agagtaatag  49500
gtcatactta tttatatgaa cactcagaaa aagagggtat gaaggttaag aaagaaatcc  49560
agtatagact aagactagga cctaaccctt attatattac taaatttact agacctcaag  49620
gatctgaatg tccagcttat ctggtacatg atttaaaatc accaacaact atctgggagg  49680
atattgaaac tattctggct ggtgaatgga ataataagcc agctaaatct ggtaaaaaaa  49740
ccagtaagaa atctggtaaa aagaaaaaat aaaaattttc taaaaatacc tttgacaacc  49800
aattaaaaat ctgataatat aaacttgtaa acaaagaggt acaatatctt gacaaatatt  49860
```

```
tatctcataa tgatatttta aaatttaagg aggacaataa catggctaaa aagactacta  49920
agagaggtaa caaaaacaaa ggaggattaa agattgatct ttcaaacgtt gaaacttcag  49980
ttactatccc agaaggaaat tacattgtgg aagtagaaga tgtagaggtt aaggtttctg  50040
aaaatagtgg aagcaattat ttatcattta cttttgtaat agcagaagga aagatgaaag  50100
gacaaaagtt ataccacatt tgctcacttc aaccacaagc tttatttaac ttaaaaggtg  50160
tgttagttgc tttaggattt gatatccctg atgaggagtt cgaattagat acagaagctc  50220
tagttggttt acaatgtgga gtagaagtat cacatgaaat atatgagggt aagaagaaat  50280
caagaataac tgattttata aaccttgacg aagctgactc tgatgatgac gaagatgagg  50340
atgatgactc agatgacgaa gaagatgatg atgaagacga tgagtctgaa gttgatcttg  50400
aagaattaga caaggatgag ctaaaagaat tagctaaggc tttaaaaatc ccagctaaga  50460
aaatcaagaa ggctaaaact gaagaagatc taattgatct aattgaagaa gaagctgacg  50520
aagaagaaat agctgaacaa tataatgacc tattcggaga ctctgatgaa gatgacgaag  50580
aagatgagga tgaagaagag gaagatgaag aagaaaatga ctatgagtca atgactttaa  50640
aagaacttaa agctgaagct aaggacagag gcttaaaggt taaaaaagga atgtctaagg  50700
atgacatcat agaaatgcta gaagaagatg atgaagaata aaatttaatt attaaaatat  50760
gagggccttt aaggtcctcc tttatttacc cttggaggct actattatgc ttgaaagaga  50820
tgtggttaaa tccataatga atatgcttaa aaaagaatac ccaggttttt ggtttaaaac  50880
tcatggggga ccctttcaaa tagctggctt acctgatata ctaggttgcc acaaaggtaa  50940
gtttattggt attgaagtta aacttcctgg aaaagaaaag aacctaactc aaaaacaaaa  51000
agacattata aataaaataa atctagcagg aggaatagct tttatggcta cctcagctga  51060
atatacaagg aggagattac atgaaaaatt tagaaagaca ccaacaattc ctaggagaac  51120
taggagatct gtatgaatta aagaataatc tatatgggga taatttccac aagacttatc  51180
ttgaatatgg aaaccctgtt ctatgtataa gacttgaaga taagctagga agagctaaaa  51240
gtttattact cggagatcaa gatgacttcc cttcatatgc tgctcaaaaa gaatctgtgg  51300
ttgatacttt actagactta gctaactatg ctattatggc tgctatggaa ctaactagtg  51360
atgataactc agaaatacat gatcttagta aagaagaata tgatgaagaa gacatagagg  51420
ataatgacga tgaggactta gatgatgaca atgtttacga cgaagaagaa ttagattttg  51480
atagtatgaa taaagaatcc ttaaaacaat atctaaaaga taatggggtt aaattccata  51540
gtaaggcctc aagagatgaa cttgtaaaac tggctaagga ggtataagga ggaggcttta  51600
atgcctcttc ttttttagta tgaagagaaa attatttaaa catcagaaag aagcattaca  51660
actattttta aataaagaaa agtttgccct atttatggac atgggtacgg gtaagacctt  51720
agtccctatt gtggcccttg agaaacttga aggtctagat actgtactaa tattctcacc  51780
taaatctatt gtatttaact gggagtctga gatccataaa tttactaaac ttaaagagta  51840
taaaatattt aaactacagg gtaataaaac caaggttatg gaaacctata gagctataaa  51900
atcctactca ggattaaaga ttattattgc caattttgag aaggctaggt tgatggataa  51960
ataccttatg aacttaaagc cacagtttat tgttgttgac gaatcccata aggtaaagaa  52020
tagaaatgcc cagatatcta aggctctata taaaattgct actaaatgta aatatagatt  52080
gataatgaca gggactccca ctcctaatgg ttatgaagat ttatttatgc aat         52133
```

UNITED STATES PATENT AND TRADEMARK OFFICE
CERTIFICATE OF CORRECTION

PATENT NO. : 9,758,767 B2
APPLICATION NO. : 14/767266
DATED : September 12, 2017
INVENTOR(S) : Bo Kyung Son et al.

It is certified that error appears in the above-identified patent and that said Letters Patent is hereby corrected as shown below:

On the Title Page

Item (56) Column 2 at Line 19, Under Other Publications, change "Niariya" to --Nariya--.

In the Specification

In Column 1 at Line 10 (Approx.), change "WO 2014/133322 Ab1" to --WO 2014/133322 A1--.

In Column 4 at Line 63, change "Seodamun-gu" to --Seodaemun-gu--.

In Column 9 at Line 57, change "Samwhaw" to --Samwha--.

In Column 9 at Line 58, change "Chungchong" to --Chungcheong--.

In Column 10 at Line 2, change "2110" to --2 mil--.

In Column 11 at Line 14, change "Seodamun-gu" to --Seodaemun-gu--.

In the Claims

In Columns 63 at Line 10 (approx.), In Claim 3, change "composition," to --composition--.

In Columns 64 at Line 2, In Claim 5, change "prepararing" to --preparing--.

In Columns 64 at Line 17, In Claim 7, change "prepring" to --preparing--.

Signed and Sealed this
Twentieth Day of February, 2018

Andrei Iancu
*Director of the United States Patent and Trademark Office*